(12) United States Patent
Thimmaiah et al.

(10) Patent No.: US 10,683,273 B2
(45) Date of Patent: Jun. 16, 2020

(54) COMPOUNDS AS DNA PROBES, METHODS AND APPLICATIONS THEREOF

(71) Applicant: JAWAHARLAL NEHRU CENTRE FOR ADVANCED SCIENTIFIC RESEARCH, Bangalore, Karnataka (IN)

(72) Inventors: Govindaraju Thimmaiah, Bengaluru (IN); Nagarjun Narayanaswamy, Bengaluru (IN)

(73) Assignee: Jawaharlal Nehru Centre for Advanced Scientific Research, Bangalore, Karnataka (IN)

(*) Notice: Subject to any disclaimer, the term of this patent is extended or adjusted under 35 U.S.C. 154(b) by 3 days.

(21) Appl. No.: 15/755,175

(22) PCT Filed: Aug. 26, 2016

(86) PCT No.: PCT/IB2016/055113
§ 371 (c)(1),
(2) Date: Feb. 26, 2018

(87) PCT Pub. No.: WO2017/033162
PCT Pub. Date: Mar. 2, 2017

(65) Prior Publication Data
US 2019/0135769 A1    May 9, 2019

(30) Foreign Application Priority Data

Aug. 26, 2015 (IN) ............................ 4493/CHE/2015

(51) Int. Cl.
| | |
|---|---|
| A61K 31/428 | (2006.01) |
| C12Q 1/6816 | (2018.01) |
| C07D 277/64 | (2006.01) |
| C07D 277/10 | (2006.01) |
| A61P 33/06 | (2006.01) |

(52) U.S. Cl.
CPC ............ *C07D 277/64* (2013.01); *A61P 33/06* (2018.01); *C07D 277/10* (2013.01); *C12Q 1/6816* (2013.01)

(58) Field of Classification Search
None
See application file for complete search history.

(56) References Cited

U.S. PATENT DOCUMENTS

2005/0208534 A1   9/2005 Dallwig et al.

OTHER PUBLICATIONS

Cosa, et al., "Photophysical Properties of Fluorescent DNA-dyes Bound to Single-and Double-stranded DNA in Aqueous Buffered Solution," Photochemistry and Photobiology, 2001, 73(6), pp. 585-599.
International Search Report from corresponding PCT Application No. PCT/IB2016/055113, dated Dec. 20, 2016, pp. 1-4.
Narayanaswamy, et al., "Sequence-specific recognition of DNA minor groove by an NIR-fluorescence switch-on probe and its potential applications," Nucleic Acids Research, 2015, vol. 43, No. 18, pp. 8651-8663.
Written Opinion from corresponding PCT Application No. PCT/IB2016/055113, dated Dec. 20, 2016, pp. 1-7.

*Primary Examiner* — Samantha L Shaterengarts
(74) *Attorney, Agent, or Firm* — Foley & Lardner LLP

(57) ABSTRACT

The present disclosure relates to the field of pharmaceutical chemistry and biotechnology. The present disclosure also relates to a compound of Formula I and a process of preparation thereof. The disclosure furthermore relates to methods/use of Formula I compounds as DNA probes. Said Formula I compounds are employed for recognizing specific DNA sequences by near Infra-red (NIR)-Fluorescence Switch-on mechanism, and have related applications including but not limited to cell imaging. Also, method of treating parasitic infections by employing the present compound of Formula I is provided.

Formula I

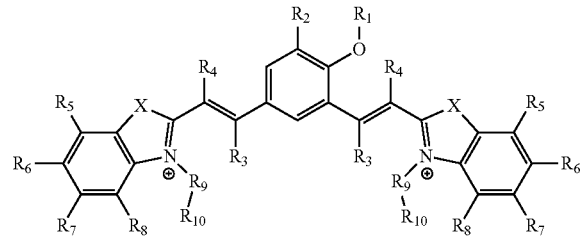

14 Claims, 16 Drawing Sheets

Specification includes a Sequence Listing.

COMPOUNDS AS DNA PROBES, METHODS AND APPLICATIONS THEREOF

CROSS-REFERENCE TO RELATED APPLICATIONS

This application is a U.S. National Phase Application under 35 U.S.C. § 371 of International Application No. PCT/IB2016/055113, filed on Aug. 26, 2016, which claims the benefit of priority to Indian Application No. 4493/CHE/2015, filed on Aug. 26, 2015, the entire contents of which are incorporated herein by reference in their entireties.

TECHNICAL FIELD

The present disclosure relates to the field of pharmaceutical chemistry and biotechnology. In particular, a compound of Formula I and a process of preparation thereof are disclosed. The disclosure further relates to methods/use of Formula I compounds as DNA probes. Said Formula I compounds are employed for recognizing specific DNA sequences by near Infra-red (NIR)-Fluorescence Switch-on mechanism, and have related applications including but not limited to cell imaging. Also, method of treating parasitic infections by employing the present compound of Formula I is provided.

SEQUENCE LISTING

The instant application contains a Sequence Listing which has been submitted electronically in ASCII format and is hereby incorporated by reference in its entirety. Said ASCII copy, created on Jul. 19, 2018, is named 056859-0289-SL.txt and is 4.82 KB in size.

BACKGROUND AND PRIOR ART OF THE DISCLOSURE

Sequence-specific recognition is an essential criterion to target and control DNA functions for gene-expression, bio-imaging, diagnostics, therapeutics and biotechnological applications. Over the years, many probes have been developed to target DNA, but there is still a pressing need for developing efficient new probes and therapeutic agents against gene-related diseases. It is a daunting task indeed to design site-specific DNA binding molecules with high affinity and selectivity. To achieve this goal, DNA binding probes ranging from small molecules to large peptides of natural and synthetic origin have been developed. These probes interact with DNA mainly through two binding modes, intercalation and groove binding. Typically, small molecules binding to DNA through intercalation possess the site-specificity of three base pairs that can differentiate only one out of 32 random sequences. Factually, the human genome contains three billion base pairs and the small molecular probe is posed with the astonishingly large number of one billion unique binding sites. To improve the binding specificity of small molecular probes over longer DNA sequences, researchers have shifted their attention towards groove-binding agents.

However, there are several disadvantages/limitations associated with the currently known small molecules/probes which interact with DNA via intercalation and/or groove binding. Some of them are, difficult synthesis processes, non-fluorescent nature limiting their potential applications in biological systems. Further, in the category of fluorescent probes, the blue fluorescence DNA staining probes (DAPI and Hoechst) require excitation in the ultraviolet (UV) region and the prolonged UV illumination is certain to damage cellular DNA. Additionally, propidium iodide and related dyes are intercalators suffering from poor cell-permeability and high toxicity, apart from inducing structural alterations in the target DNA structure, which prohibits their use in biological applications.

The availability of myriad genome data warrants the need for developing efficient and highly predictive molecular tools to probe its organization and functional aspects. Overall, it is clear that sequence-specific targeting of DNA is crucial for studying sequence variation, structural organization and function in the cell nucleus. However, existing probes suffer from various limitations and there is a persistent need to develop probes with superior properties. Especially, fluorescence DNA probes must satisfy the following properties: i) excitation and emission in the longer wavelength region, ii) switch-on fluorescence response, iii) high sequence-specificity, iv) good quantum yield, v) non-toxicity to human cells, and vi) live-cell permeability.

The present disclosure addresses the need by providing potent small molecule probes having superior properties, the process for synthesis of said small molecules and related methods and applications thereof.

BRIEF DESCRIPTION OF ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

FIG. 1 depicts (a) Molecular structure of QCy-DT and activation of QCy-DT to form 'NIR-ready' fluorescence probe (Cy7 system); (b) The absorbance and emission spectra of QCy-DT in buffer solution (Tris-HCl, 100 mM, pH=7.4); (c) DNA minor groove recognition of QCy-DT through switch-on NIR-fluorescence response.

FIG. 2 depicts photophysical properties of QCy-DT. (a) Absorption spectra of QCy-DT (2 µM) with increasing concentration of Drew-AT (0, 1, 2, 3 and 4 µM); (b) Fluorescence spectrum of QCy-DT (2 µM) in the presence of Drew-AT (4 µM). (c) Fluorescence spectra of Drew-AT (4 µM) with increasing concentration of QCy-DT (0 to 10 µM), Inset: Shows the plot of fluorescence intensity as a function of the concentration of QCy-DT. (d) Fluorescence titration curve of QCy-DT with increasing concentration of Drew-AT (0 to 5 µM). Inset: Job plot of QCy-DT with Drew-AT, which show 1:1 binding stoichiometry.

(b) Plot of fluorescence intensity of QCy-DT ratio against the variable (A/T)$_4$ sequence. (c) Plot of fluorescence intensity ratio of QCy-DT against local variations around 5'-X (AATT)Y-3' sequences.

Figure 6:
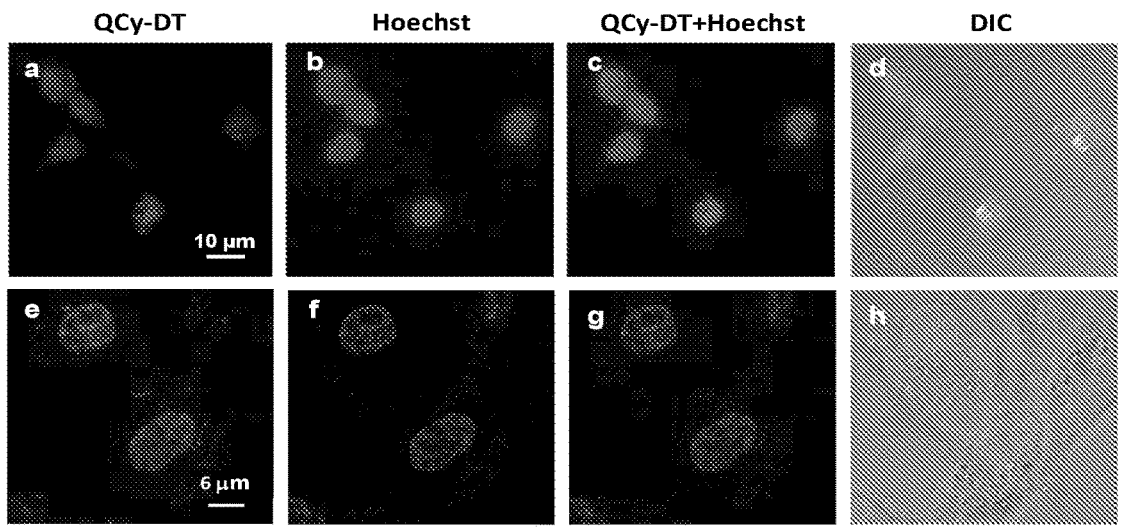

FIG. 6 depicts cellular uptake properties of QCy-DT in live MCF-7 and fixed HeLa cells. (a-d) Fluorescence microscope images of live MCF-7 cells incubated with QCy-DT. a: QCy-DT (0.5 µM), b: Hoechst (0.5 µM), c: overlay image of a and b, d: differential interference contrast (DIC, bright field image) with overlay of a and b. (e-h) Confocal microscope images of fixed HeLa cells incubated with QCy-DT. e: QCy-DT (0.5 µM), f: Hoechst (0.5 µM), g: overlay image of e and f, h: differential interference contrast (DIC, bright field image) with overlay of e and f. Images are collected from 600-800 nm upon excitation at 520 nm.

Figure 7:
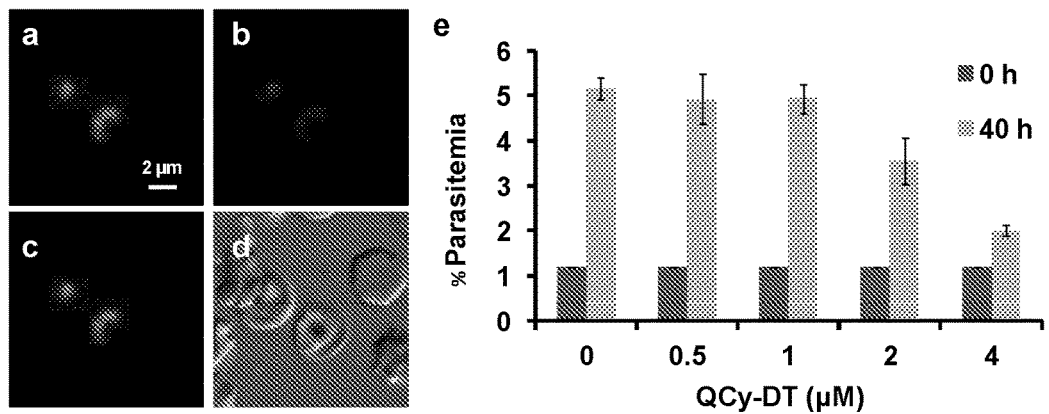

FIG. 7 depicts the uptake of QCy-DT in live *Plasmodium falciparum* parasites. (a-d) Fluorescence microscope images of blood stages of *Plasmodium falciparum* incubated with QCy-DT. a: QCy-DT (0.5 µM), b: DAPI, c: Overlay of images of a and b, d: differential interference contrast (DIC, bright field image) with overlay of a and b. Fluorescence images are collected from 600-720 nm upon excitation at 520 nm. (e) IC$_{50}$ determination of QCy-DT in malaria parasites. A concentration range of 0, 0.5, 1, 2 and 4 µM of QCy-DT is used. The graphs are plotted for the percentage of parasitemia [at the beginning of the experiment, 0 h (~20 h; early trophozoite stage parasites) and following 40 h of incubation with QCy-DT when the control parasites have entered the next cycle of invasion] against QCy-DT concentration, with mean and standard error.

Figure 8:
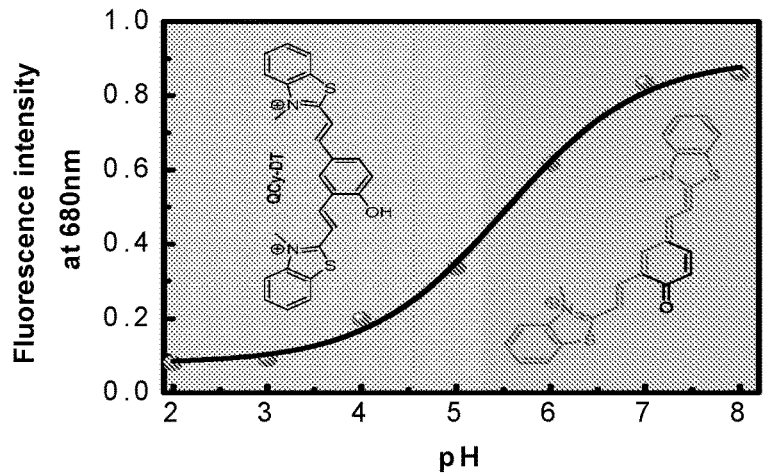

FIG. 8 depicts the plot of fluorescence intensity of QCy-DT at 680 nm as function of solution pH upon excitation at 530 nm.

Figure 9:
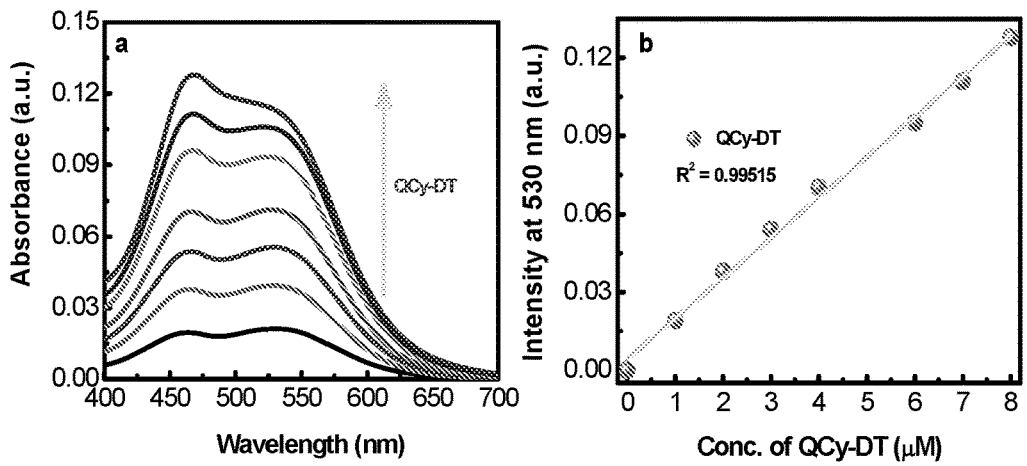

FIG. 9 depicts the absorption spectra of QCy-DT. (a) Absorption spectra of QCy-DT with increasing concentration from 0 to 8 µM in Tris-HCl buffer solution (100 mM, pH=7.4). (b) Plot of absorption intensity at 530 nm against the concentration of QCy-DT.

Figure 10:
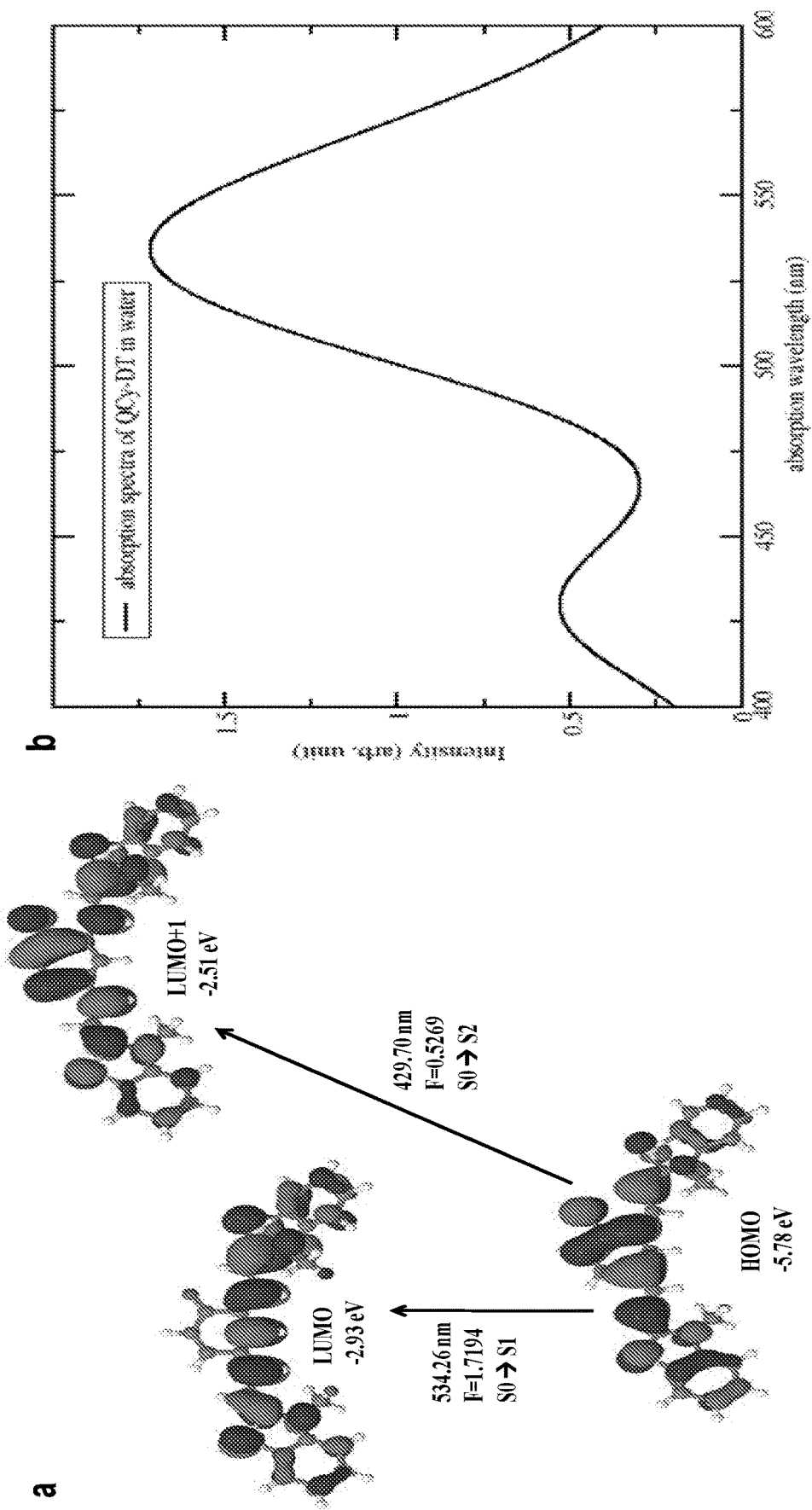

FIG. 10 depicts optical transitions of QCy-DT. (a) Molecular orbitals involved in the S1 and S2 electronic transitions for QCy-DT in water. (b) Computed absorption spectra for QCy-DT in water.

Figure 11:
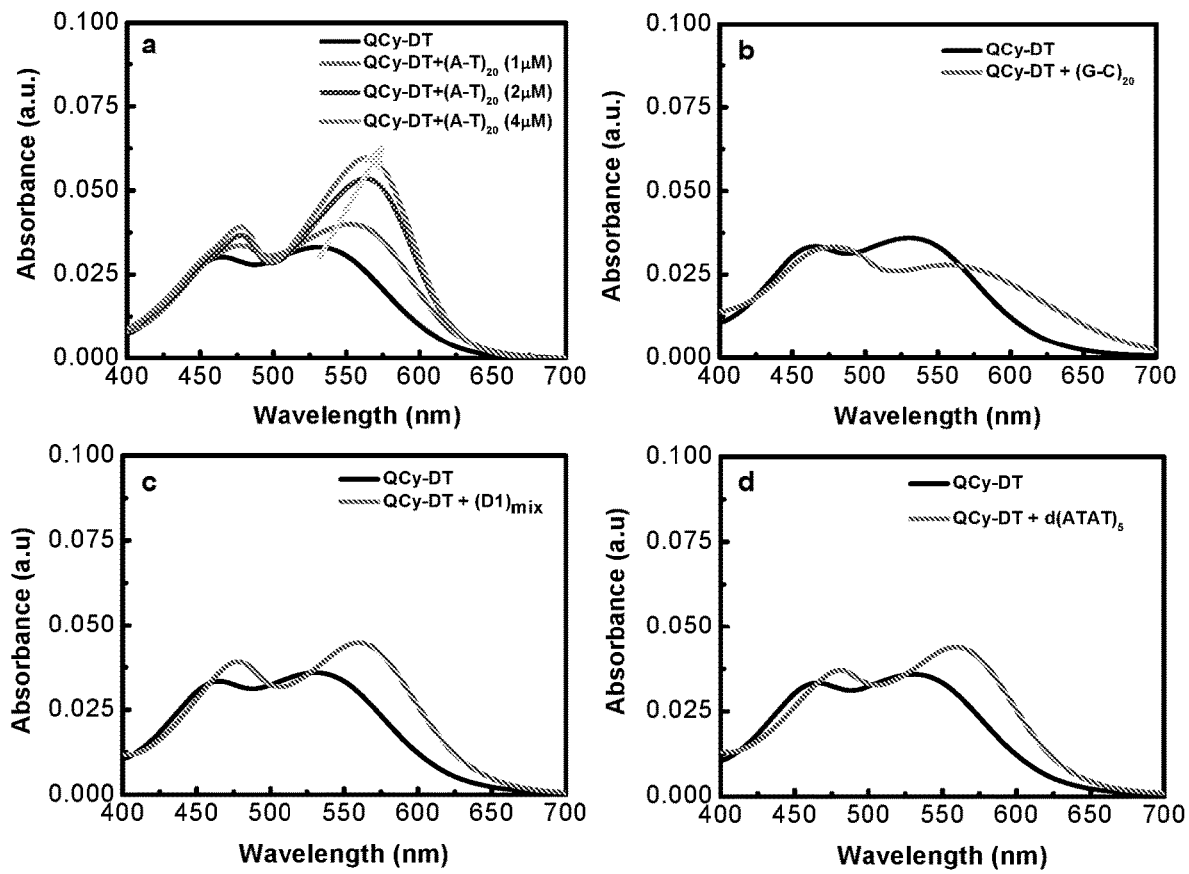

FIG. 11 depicts absorption spectra of QCy-DT in presence of various DNA duplexes. (a) Absorption spectra of QCy-DT (2 µM) with increasing concentration of (A-T)$_{20}$ from 0 to 4 µM. (b-d) are absorption spectra of QCy-DT (2 µM) in presence of (G-C)$_{20}$, (D1)$_{mix}$ and d(ATAT)$_5$ (4 µM) respectively, in Tris-HCl buffer solution.

Figure 12:
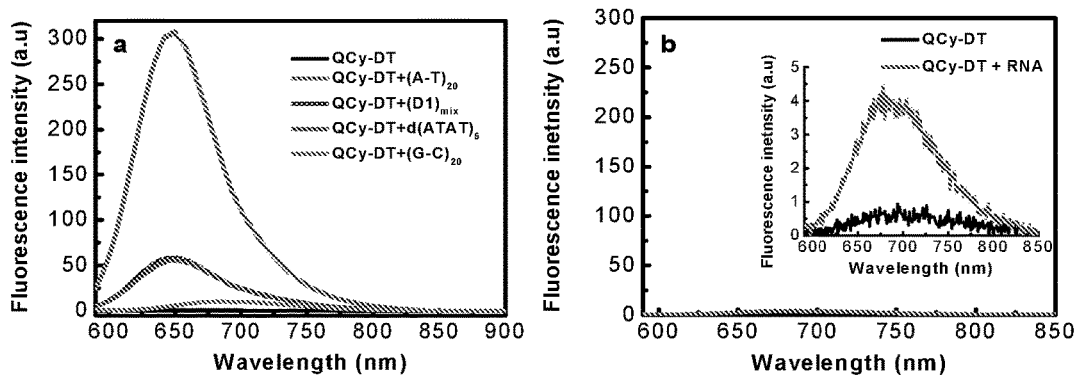

FIG. 12 depicts (a) Fluorescence spectra of QCy-DT (2 µM) in presence of DNA duplex (4 µM) in Tris-HCl buffer solution; (b) Fluorescence spectra of QCy-DT (2 µM) in presence of RNA (4 µM) in Tris-HCl buffer solution.

Figure 13:
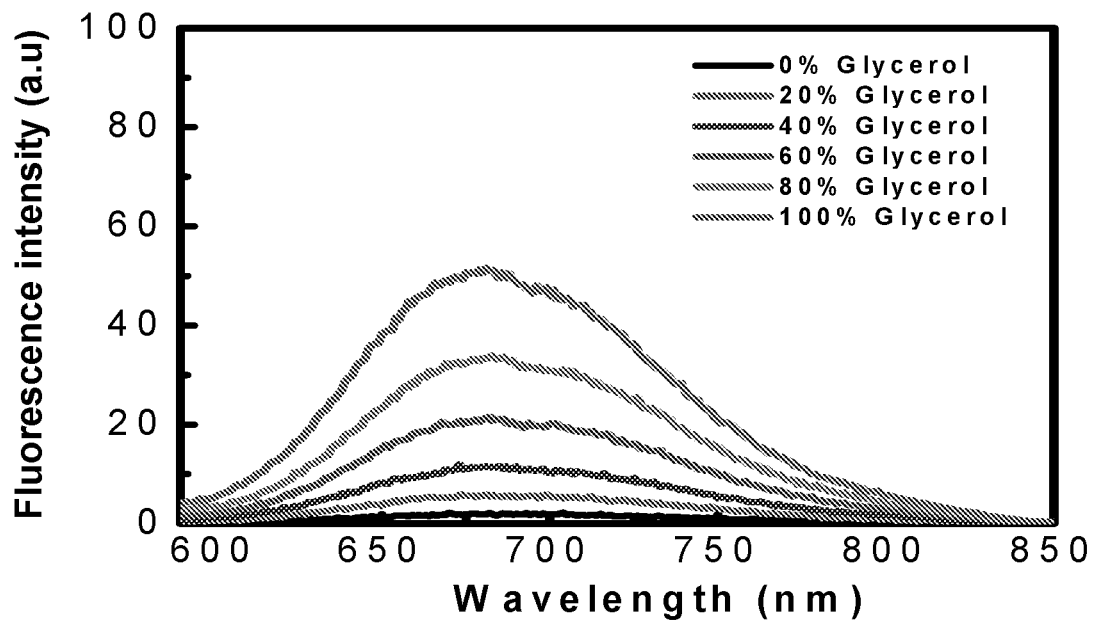

FIG. 13 depicts fluorescence spectra of QCy-DT (2 µM) with increasing glycerol content from 0 to 100% in Tris-HCl buffer solution.

Figure 14:
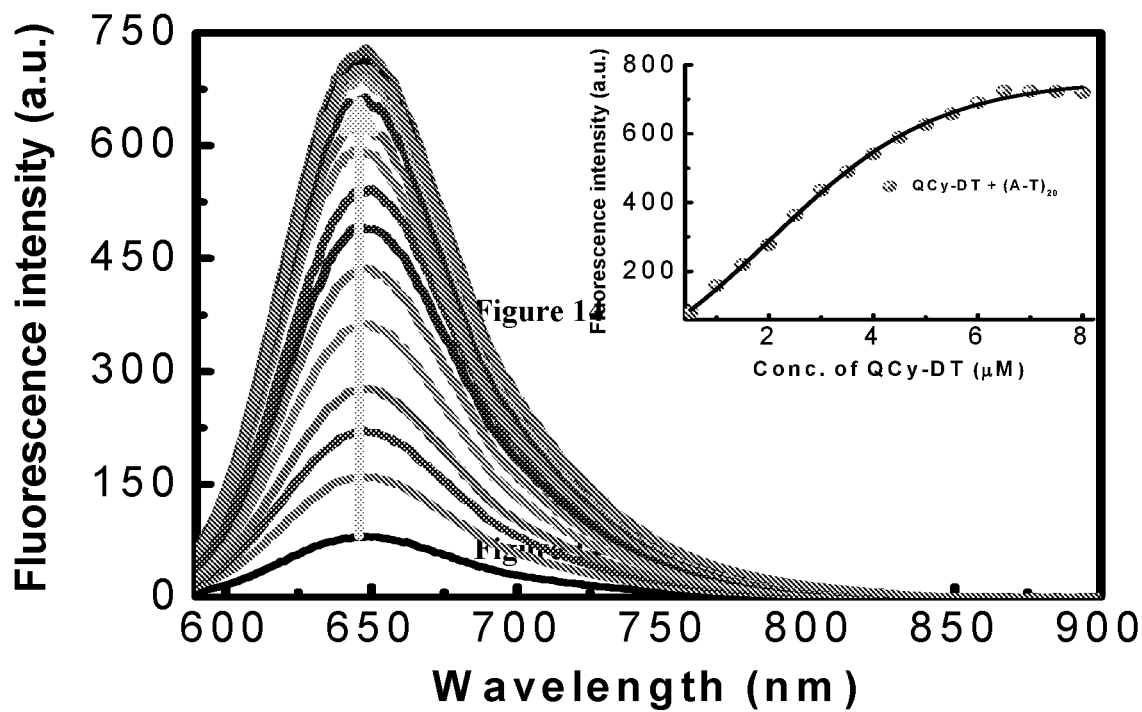

FIG. 14 depicts fluorescence spectra of (A-T)$_{20}$ with increasing concentration of QCy-DT from 0 to 8 µM. Inset: Plot of fluorescence intensity at 650 nm as function of QCy-DT concentration.

Figure 15:
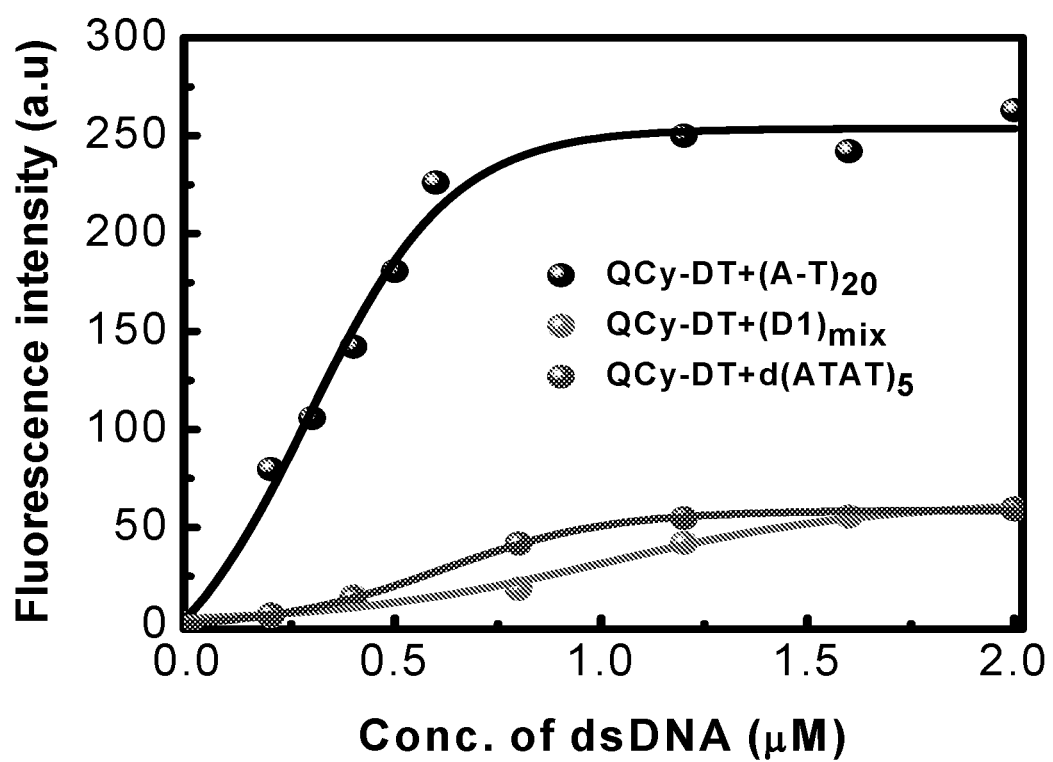

FIG. 15 depicts fluorescence spectra of QCy-DT (2 µM) with increasing concentration of DNA duplexes (A-T)$_{20}$, (D1)$_{mix}$ and d(ATAT)$_5$ from 0 to 2 µM in buffer solution.

Figure 16:
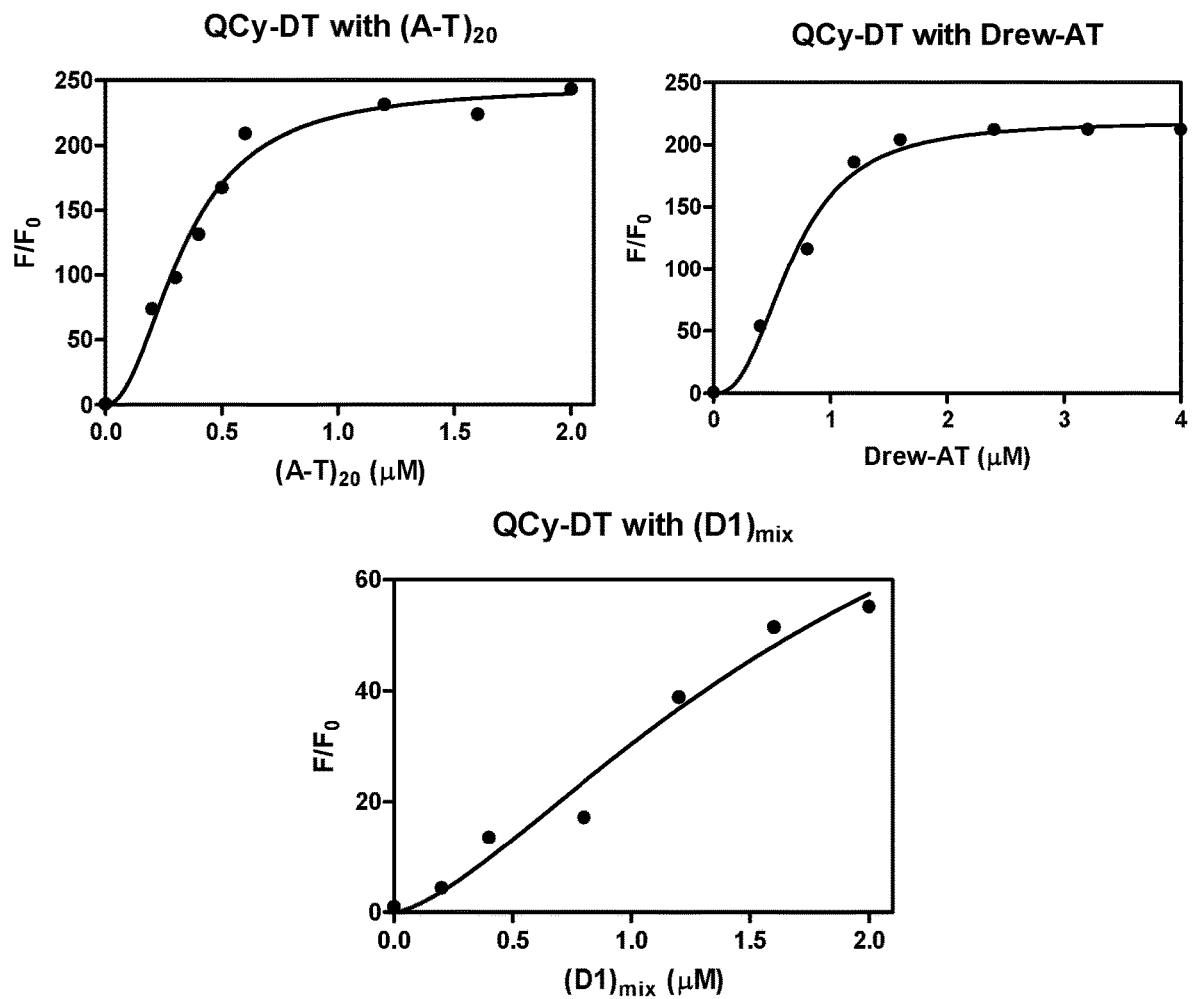

FIG. 16 depicts Fluorescence titration curves of QCy-DT (2 µM) in presence of DNA duplexes (A-T)$_{20}$, Drew-AT and (D1)$_{mix}$ in buffer solution.

Figure 17:
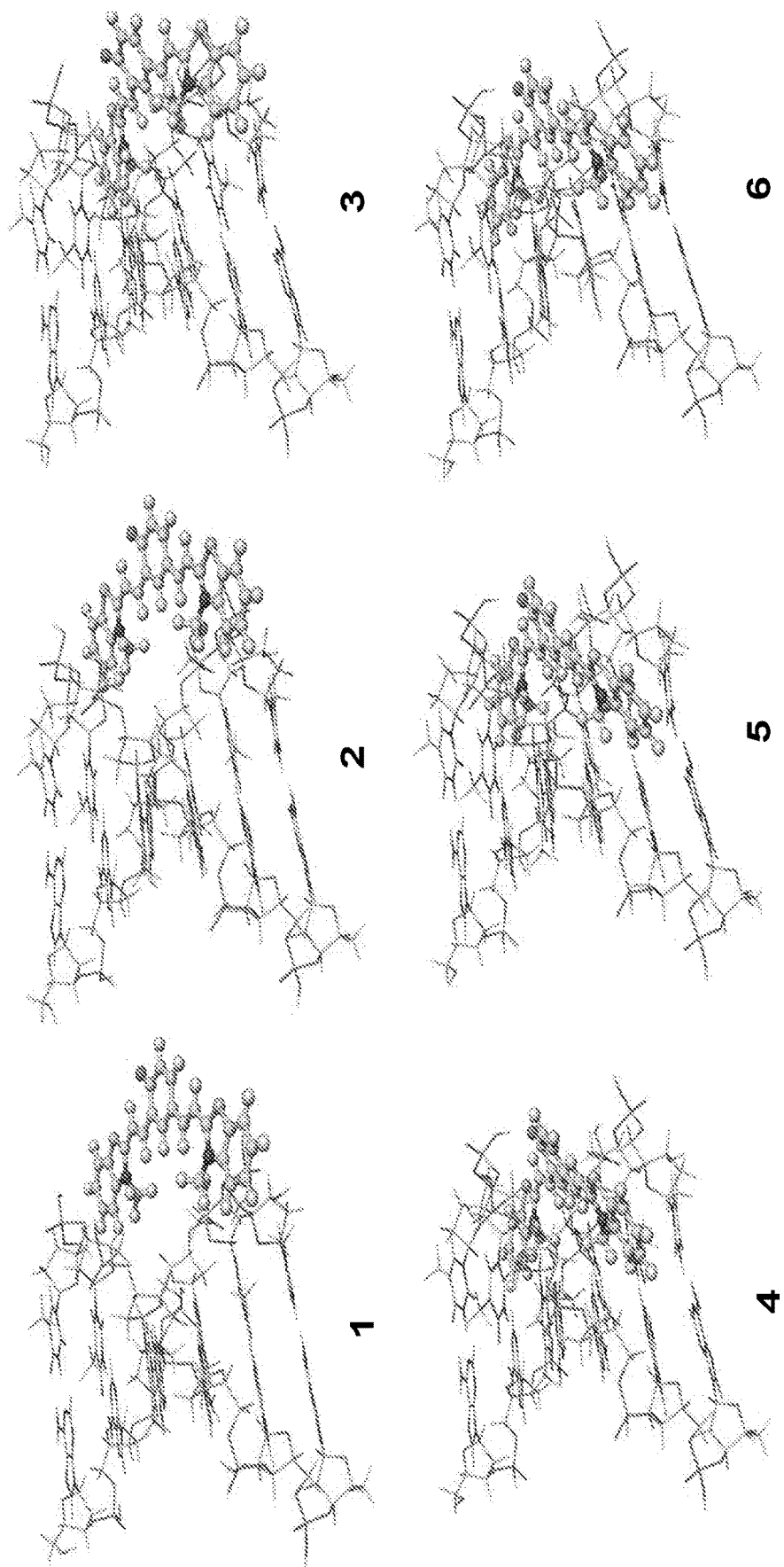

FIG. 17 depicts snapshots of optimization process of 5'-AAATTT-3'/QCy-DT complex.

Figure 18:
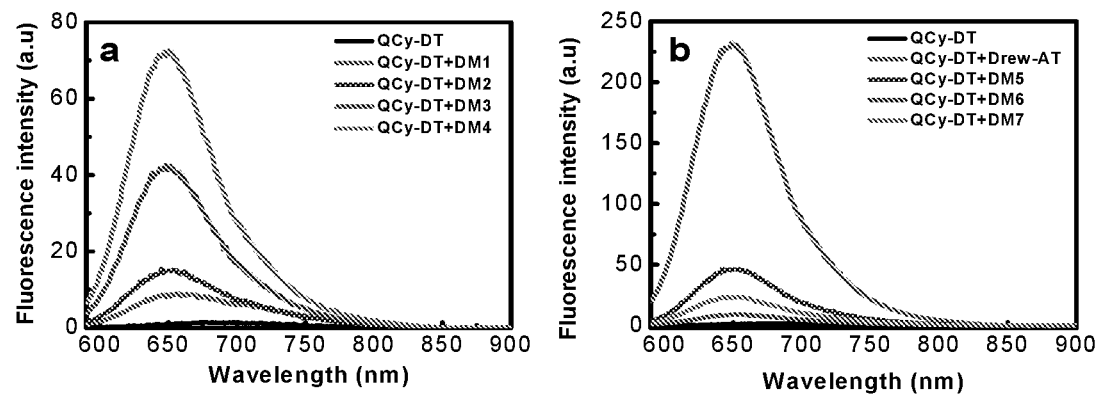

FIG. 18 depicts Fluorescence spectra of QCy-DT (2 µM) in presence of AT-rich sequences. (a) Fluorescence spectra of QCy-DT (2 µM) in presence of DM1, DM2, DM3 and DM4 duplexes (each 4 µM). (b) Fluorescence spectra of QCy-DT (2 µM) in presence of DM5, DM6, DM7 and Drew-AT (each 4 µM) duplexes in Tris-HCl buffer solution.

Figure 19:
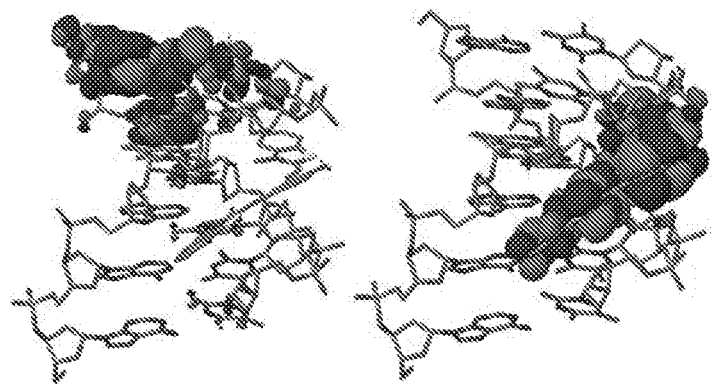

FIG. 19 depicts relevant molecular orbitals involved in optical transitions of 5'-AAATTT-3'/QCy-DT complex.

Figure 20:
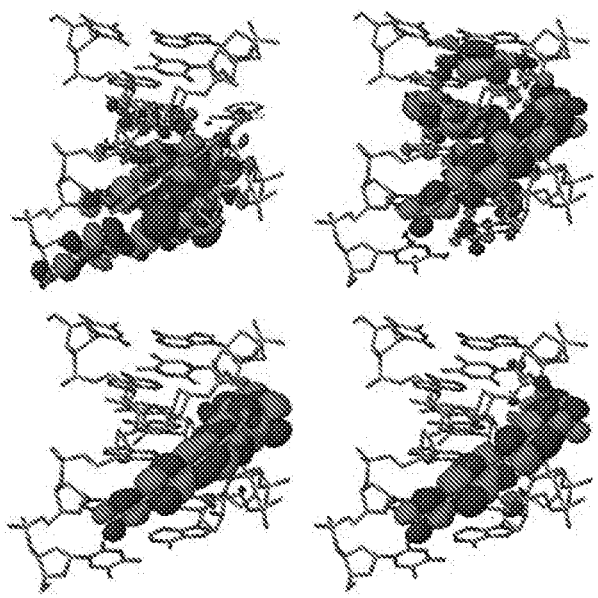

FIG. 20 depicts relevant molecular orbitals involved in optical transitions of 5'-TAATTA-3'/QCy-DT complex.

Figure 21:
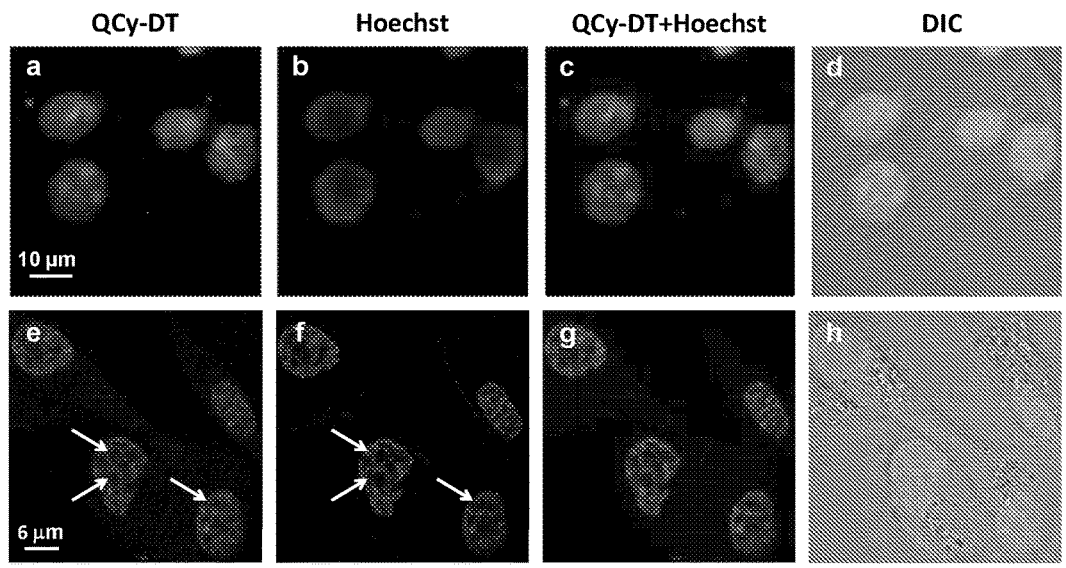

FIG. 21 depicts Cellular uptake properties of QCy-DT in live MCF-7 and fixed HeLa cells. (a-d) Fluorescence microscope images of live MCF-7 cells incubated with QCy-DT. a: QCy-DT (1 µM), b: Hoechst (1 µM), c: overlay image of a and b, d: differential interference contrast (DIC, bright field image) with overlay of a and b. (e-h) Confocal microscope images of fixed HeLa cells incubated with QCy-DT. e: QCy-DT (1 µM), f: Hoechst (1 µM), g: overlay image of e and f, h: differential interference contrast (DIC, bright field image) with overlay of e and f. Arrows indicates the black nucleoli, which is characteristic feature of specific DNA minor groove binders. Images are collected from 600-720 nm upon excitation at 520 nm.

Figure 22:
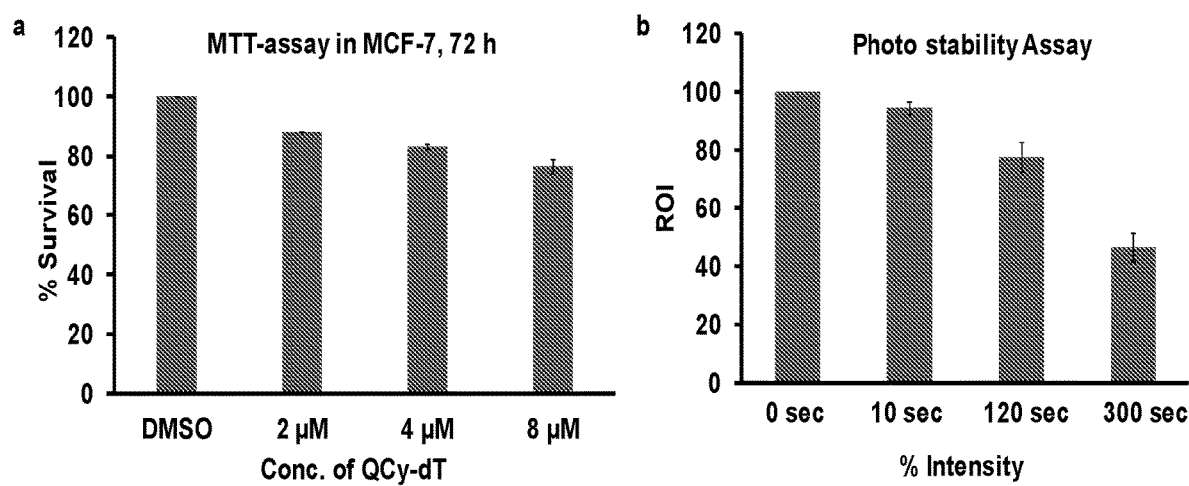

FIG. 22 depicts (a) Cell viability of MCF-7 cells in presence of QCy-DT in dose dependent manner by taking 2 µM, 4 µM and 8 µM of probe QCy-DT. Mean±SEM. (b) Photostability of QCy-DT (2 µM) in MCF-7 cells by continuous scanning using OLYMPUS FV1000 confocal microscope, under 568 nm line of an argon ion laser for different time durations, 10 sec, 120 sec and 300 sec respectively. Representative images are shown with graph for mean intensity at different time points with standard error.

Figure 23:
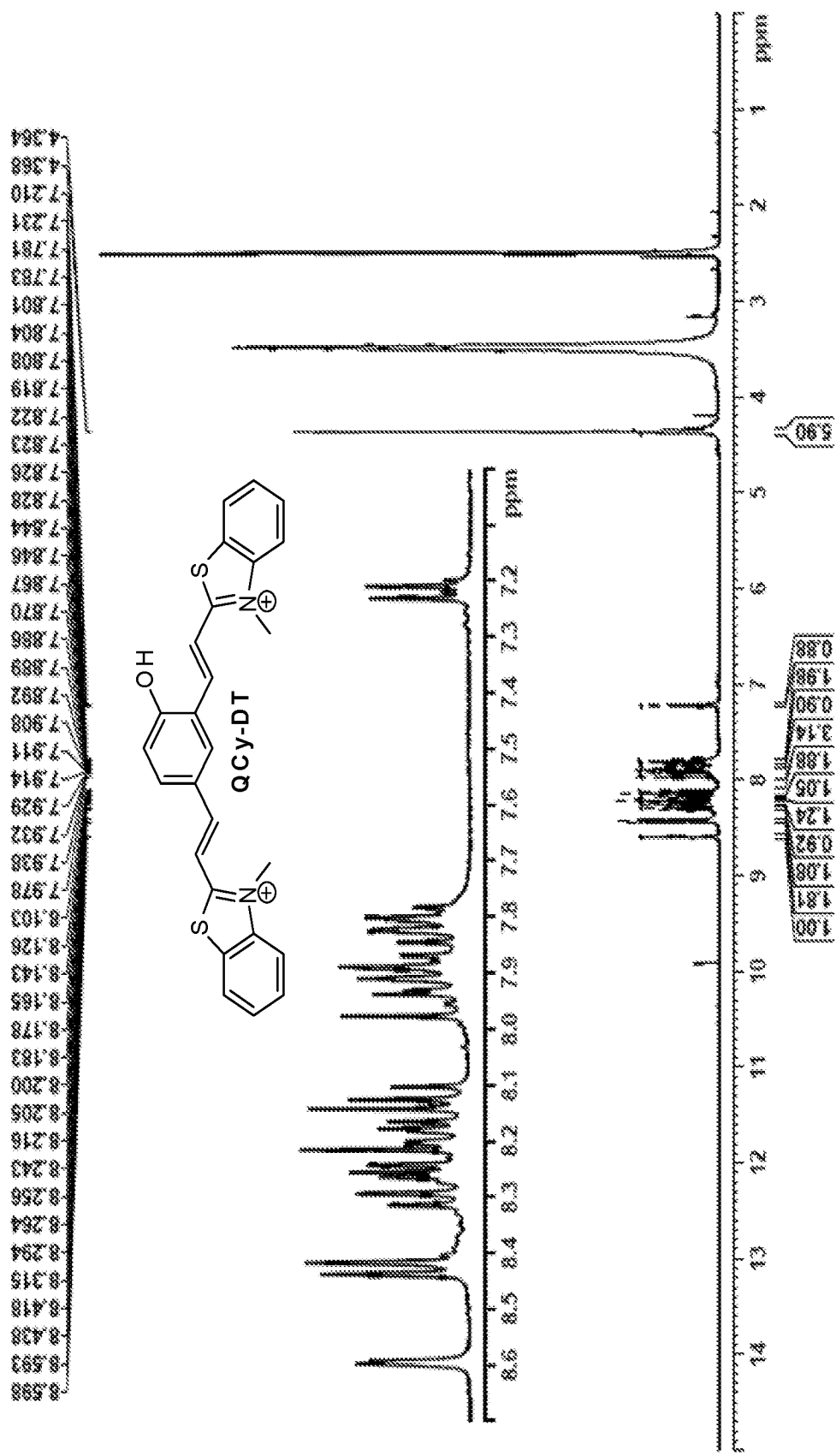

FIG. 23 depicts $^1$H NMR spectrum of QCy-DT.

Figure 24:
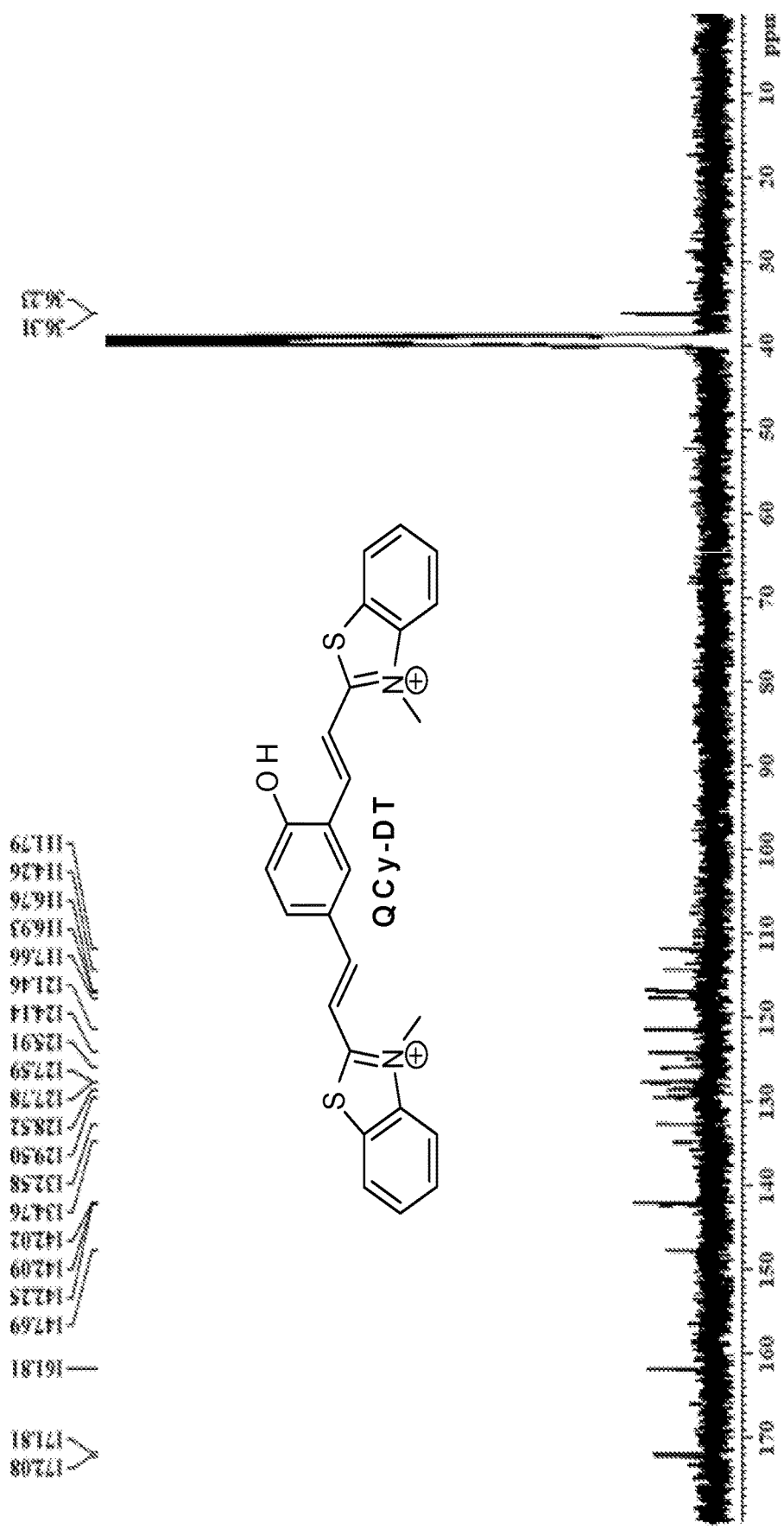

FIG. 24 depicts $^{13}$C NMR spectrum of QCy-DT.

STATEMENT OF THE DISCLOSURE

The present disclosure relates to a compound of Formula I

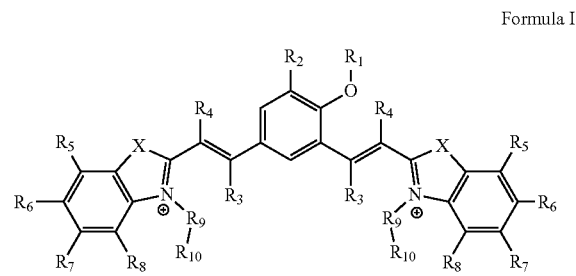

Formula I wherein, 'X' is selected from a group comprising oxygen, sulphur, and selenium;
'R$_1$' is hydrogen;
'R$_2$' is selected from a group comprising H, OH, halogen, alkyl and substituted alkyl, and wherein, the halogen is selected from a group comprising bromide, chloride and iodide;
'R$_3$' and 'R$_4$' is independently selected from a group comprising H, alkyl, aryl, nitrile, acid and halogen, and wherein the halogen is selected from a group comprising, chloride, fluoride, bromide and iodide;
'R$_5$', 'R$_6$', 'R$_7$' and 'R$_8$' are independently selected from a group comprising H, OH, alkyl, aryl, halogen, nitro, sulfonates (SO$_3^-$) and nitrile;

'R$_9$' is selected from a group comprising H and —(CH$_2$)$_n$—, wherein 'n' is 1-6;

'R$_{10}$' is selected from a group comprising hydrogen, —OH, methyl, amine, terminal alkyne, alkene, alkyl acid, amine acid and sulfonates (SO$_3^-$);

or its derivative, tautomer, isomer, polymorph, solvate or intermediate thereof;

a compound of Formula I according to claim 1 selected from

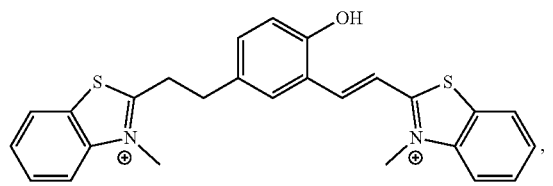

QCy-DT

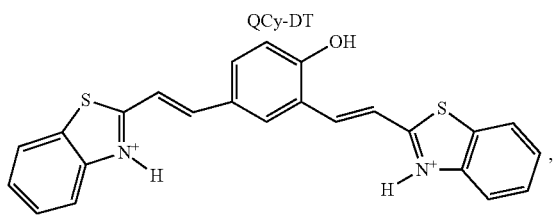

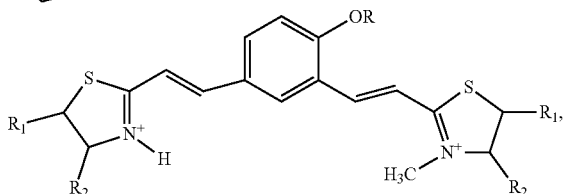

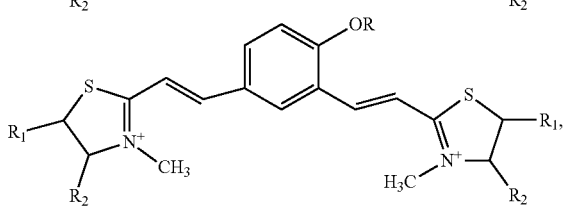

R, R$_1$, R$_2$=any alky aryl or heterocyclic substituents or cyclic structure

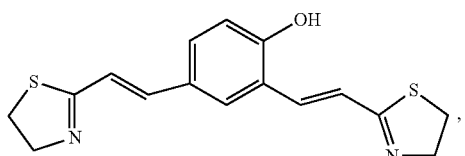

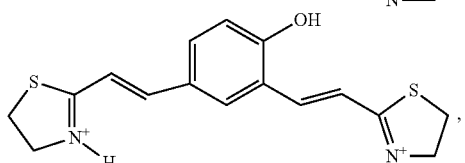, and

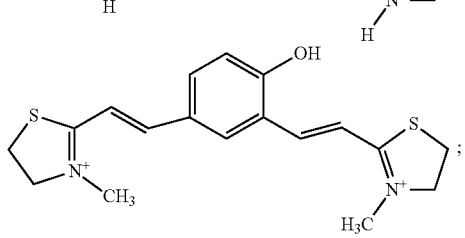;

a process for preparation of a compound of Formula I:

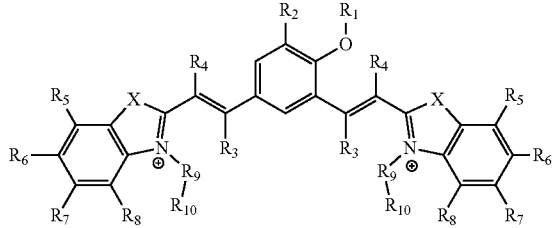

Formula I wherein, 'X' is selected from a group comprising oxygen, sulphur, and selenium;

'R$_1$' is hydrogen;

'R$_2$' is selected from a group comprising H, OH, halogen, alkyl and substituted alkyl, and wherein, the halogen is selected from a group comprising bromide, chloride and iodide;

'R$_3$' Or 'R$_4$' is selected from a group comprising H, alkyl, aryl, nitrile, acid and halogen, and wherein the halogen is selected from a group comprising, chloride, fluoride, bromide and iodide;

'R$_5$', 'R$_6$', 'R$_7$' or 'R$_8$' is selected from a group comprising H, OH, alkyl, aryl, halogen, nitro, sulfonates (SO$_3^-$) and nitrile group;

'R$_9$' is selected from a group comprising H and —(CH$_2$)$_n$—, wherein 'n' is 1-6;

'R$_{10}$' is selected from a group comprising hydrogen, —OH, methyl, amine, terminal alkyne, alkene, alkyl acid, amine acid and sulfonates (SO$_3^-$); or any derivative, tautomeric form, isomer, polymorph, solvate and intermediates thereof;

said process comprising:

a. reacting compound of Formula II with compound of Formula III to obtain compound of Formula IV

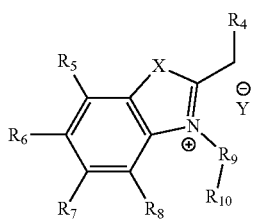

Formula IV wherein,

'R$_4$' is selected from a group comprising H, alkyl, aryl, nitrile, acid and halogen, and wherein the halogen is selected from a group comprising, chloride, fluoride, bromide and iodide;

'R$_5$', 'R$_6$', 'R$_7$' or 'R$_8$' is selected from a group comprising H, OH, alkyl, aryl, halogen, nitro, sulfonates (SO$_3^-$) and nitrile group;

'R$_9$' is selected from a group comprising H and —(CH$_2$)$_n$—, wherein 'n' is 1-6; and 'R$_{10}$' is selected from a group comprising hydrogen, —OH, methyl, amine, terminal alkyne, alkene, alkyl acid, amine acid and sulfonates (SO$_3^-$);

'Y' is either Br or I;

Formula II

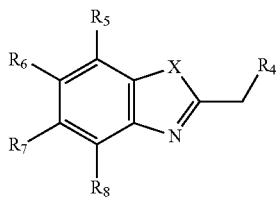

wherein,

'R₄' is selected from a group comprising H, alkyl, aryl, nitrile, acid and halogen, and wherein the halogen is selected from a group comprising, chloride, fluoride, bromide and iodide; and 'R₅', 'R₆', 'R₇' or 'R₈' is selected from a group comprising H, OH, alkyl, aryl, halogen, nitro, sulfonates (SO₃⁻) and nitrile group;

Formula III

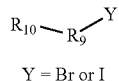

Y = Br or I wherein,

'R₉' is selected from a group comprising H and —(CH₂)$_n$—, wherein 'n' is 1-6;

'R₁₀' is selected from a group comprising hydrogen, —OH, methyl, amine, terminal alkyne, alkene, alkyl acid, amine acid and sulfonates (SO₃⁻);

and, b. reacting the compound of Formula IV with compound of Formula V in presence of piperidine and alcohol, Formula V

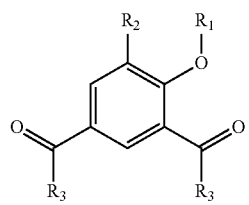

wherein,

'R₁' is hydrogen;

'R₂' is selected from a group comprising H, OH, halogen, alkyl and substituted alkyl, and wherein, the halogen is selected from a group comprising bromide, chloride and iodide; and 'R₃' is selected from a group comprising H, alkyl, aryl, nitrile, acid and halogen, and wherein the halogen is selected from a group comprising, chloride, fluoride, bromide and iodide;

a pharmaceutical composition comprising a compound of Formula I:

Formula I

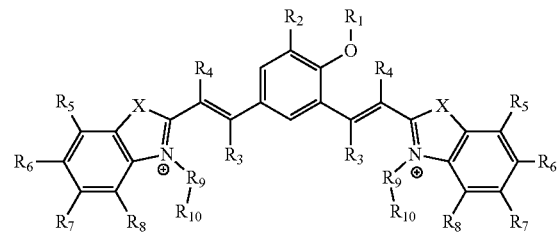

any derivative, tautomeric form, isomer, polymorph, solvate and intermediates thereof;

wherein, 'X' is selected from a group comprising oxygen, sulphur, and selenium;

'R₁' is hydrogen;

'R₂' is selected from a group comprising H, OH, halogen, alkyl and substituted alkyl, and wherein, the halogen is selected from a group comprising bromide, chloride and iodide;

'R₃' or 'R₄' is selected from a group comprising H, alkyl, aryl, nitrile, acid and halogen, and wherein the halogen is selected from a group comprising, chloride, fluoride, bromide and iodide;

'R₅', 'R₆', 'R₇' or 'R₈' is selected from a group comprising H, OH, alkyl, aryl, halogen, nitro, sulfonates (SO₃⁻) and nitrile group;

'R₉' is selected from a group comprising H and —(CH₂)$_n$—, wherein 'n' is 1-6;

'R₁₀' is selected from a group comprising hydrogen, —OH, methyl, amine, terminal alkyne, alkene, alkyl acid, amine acid and sulfonates (SO₃⁻);

optionally along with at least one pharmaceutically acceptable excipient;

a method of detection or quantification of DNA sequence, said method comprising:

a. contacting the probe of compound of Formula I or its derivative, tautomer, isomer, polymorph, solvate or intermediates thereof, or the composition comprising compound of formula I with a DNA or peptide sequence so as to allow for hybridization of the probe with the DNA or peptide sequence; and b. detecting or quantifying the binding intensity by measuring the change in fluorescence of the probe resulting from the specific interaction or binding of the probe to DNA or peptide sequence, upon hybridization of the probe to DNA or peptide sequence;

a method of inhibiting growth of a cell, said method comprising contacting the compound of Formula I or its derivative, tautomer, isomer, polymorph, solvate or intermediates thereof, or the composition comprising compound of formula I with the cell;

a method of managing or treating a disease or an infection in a subject, said method comprising step of administering the compound of Formula I as claimed in claim 1 or any derivative, tautomer, isomer, polymorph, solvate or its intermediates thereof, or the composition comprising compound of formula I in said subject to manage and treat the disease or the infection;

use of the compound of Formula I or any derivative, tautomeric form, isomer, polymorph, solvate and intermediates thereof, or the composition comprising compound of formula I for detecting or quantifying the presence of specific DNA or peptide sequence, in particular AT-rich DNA sequence, inhibiting growth of cells or a combination thereof, and for in-vitro and in-vivo cell imaging;

use of compound of Formula I as claimed in claim 1 or any derivative, tautomer, isomer, polymorph, solvate or its intermediates thereof, or the composition comprising compound of formula I in the manufacture of a medicament for treatment of parasitic infection or in the manufacture of stimuli responsive probes; and a method of diagnosing disease characterized by presence of specific DNA or peptide sequence or abnormal levels of AT rich DNA, the method comprising:
  a. contacting the probe of compound of Formula I with a biological sample comprising DNA or peptide sequence to allow for hybridization of the probe with the DNA or peptide sequence or antibodies;
  b. removing the unhybridized probe from the mixture; and
  c. detecting or quantifying the presence of specific DNA or peptide sequence, by measuring the change in fluorescence of the probe resulting from the specific interaction or binding of the probe to DNA, upon hybridization of the probe to DNA to diagnose the disease.

DETAILED DESCRIPTION OF THE DISCLOSURE

The present disclosure relates to a compound of Formula I, synthesis and methods/applications thereof.

Formula I

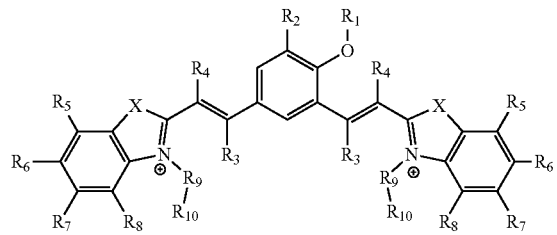

wherein, 'X' is selected from a group comprising oxygen, sulphur, and selenium;
  '$R_1$' is hydrogen;
  '$R_2$' is selected from a group comprising H, OH, halogen, alkyl and substituted alkyl, and wherein, the halogen is selected from a group comprising bromide, chloride and iodide;
  '$R_3$' Or '$R_4$' is selected from a group comprising H, alkyl, aryl, nitrile, acid and halogen, and wherein the halogen is selected from a group comprising, chloride, fluoride, bromide and iodide;
  '$R_5$', '$R_6$', '$R_7$' or '$R_8$' is selected from a group comprising H, OH, alkyl, aryl, halogen, nitro, sulfonates ($SO_3^-$) and nitrile group;
  '$R_9$' is selected from a group comprising H and —$(CH_2)_n$—, wherein 'n' is 1-6;
  '$R_{10}$' is selected from a group comprising hydrogen, —OH, methyl, amine, terminal alkyne, alkene, alkyl acid, amine acid and sulfonates ($SO_3^-$).

In an embodiment of the present disclosure, tautomers, isomers, analogs, derivatives and salts of Formula I compounds are also provided.

In an exemplary embodiment of the present disclosure, the Formula I compound is quinone cyanine-dithiazole (QCy-DT).

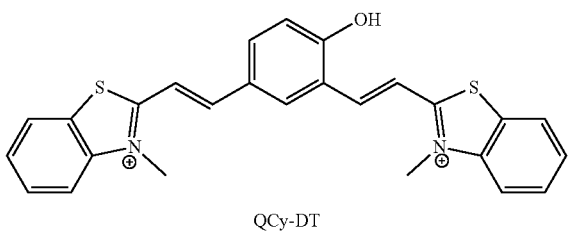

QCy-DT

In another embodiment, of the present disclosure, compound of Formula I is selected from

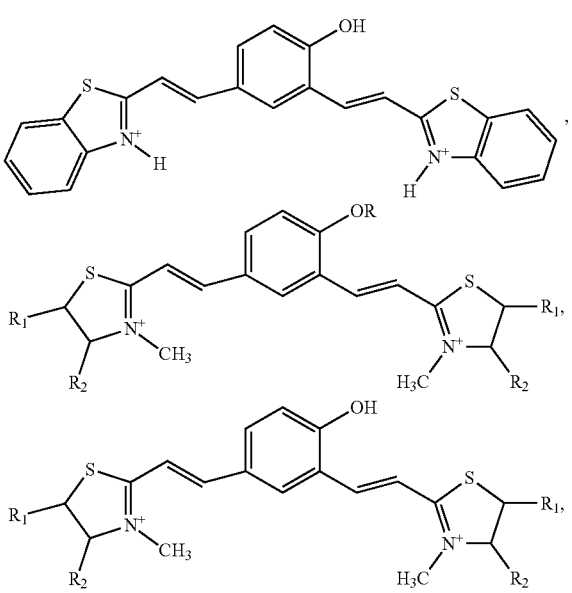

R, $R_1$, $R_2$=any alky aryl or heterocyclic substituents or cyclic structure

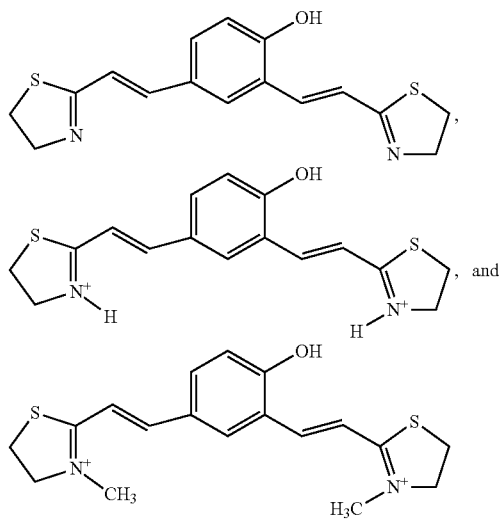

In an embodiment of the present disclosure, compound of Formula I, particularly, QCy-DT is a bent-shaped molecular probe, a D2A (one-donor-two-acceptor) π-electron system which undergoes internal charge transfer to convert itself into a switch-on NIR-fluorophore upon binding to DNA (FIG. 1). The bent shaped QCy-DT obeys isohelicity and recognizes the minor groove of duplex DNA with switch-on near Infra-red (NIR)-fluorescence response. Remarkably, fluorescence and circular dichroism (CD) studies reveal that QCy-DT binding to AT-rich DNA minor groove results in switch-on NIR-emission in a sequence-specific manner, especially with a 5'-A<u>AATT</u>T-3' sequence. Most of the desirable properties such as large Stokes shift, switch-on fluorescence (non-aggregated and non-fluorescent in unbound-state but emit NIR-fluorescence in DNA bound-state), and sequence-specific binding of QCy-DT in buffer solution demonstrate its superiority as a DNA probe. The live cell imaging studies confirm low-toxicity, high cell permeability, effective nuclear DNA staining and photostability by QCy-DT at low concentration (≤1 M, preferably about 0.5 µM to 1 µM) without the need of RNase treatment. Uptake of QCy-DT by *Plasmodium* nucleus at a very low concentration of 500 nM (preferably about 0.5 µM to 1 µM) and a low (<4 M, preferably about 3 µM to 4 µM) inhibitory concentration ($IC_{50}$) against malarial parasites proves that Formula compounds have therapeutic applications, particularly in treating parasitic infections.

Thus, the present disclosure provides sequence-specific recognition of DNA minor groove by switch-on NIR-fluorescence probes of Formula I. Formula I compounds display high sequence-specificity (5'-A<u>AATT</u>T-3') for DNA minor groove and is an improved/effective probe for nuclear DNA staining of live and fixed mammalian cells, among other molecular, cell biology and medical applications including treatment of infections.

The present disclosure also relates to a process for preparation of compound of Formula I

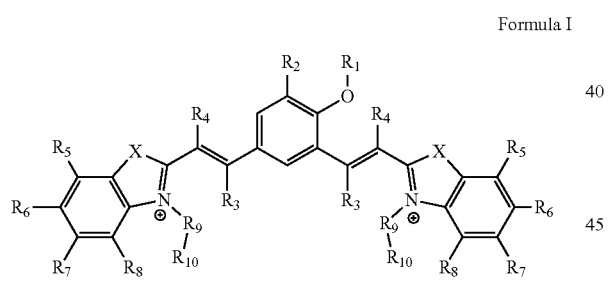

Formula I wherein, 'X' is selected from a group comprising oxygen, sulphur, and selenium;
'$R_1$' is hydrogen;
'$R_2$' is selected from a group comprising H, OH, halogen, alkyl and substituted alkyl, and wherein, the halogen is selected from a group comprising bromide, chloride and iodide;
'$R_3$' Or '$R_4$' is selected from a group comprising H, alkyl, aryl, nitrile, acid and halogen, and wherein the halogen is selected from a group comprising, chloride, fluoride, bromide and iodide;
'$R_5$', '$R_6$', '$R_7$' or '$R_8$' is selected from a group comprising H, OH, alkyl, aryl, halogen, nitro, sulfonates ($SO_3^-$) and nitrile group;
'$R_9$' is selected from a group comprising H and —($CH_2$)$_n$—, wherein 'n' is 1-6;
'$R_{10}$' is selected from a group comprising hydrogen, —OH, methyl, amine, terminal alkyne, alkene, alkyl acid, amine acid and sulfonates ($SO_3^-$); or any derivative, tautomeric form, isomer, polymorph, solvate and intermediates thereof;

said process comprising:
b. reacting compound of Formula II with compound of Formula III to obtain compound of Formula IV

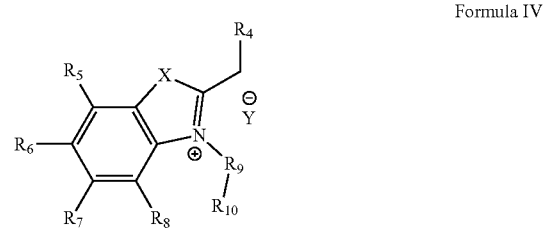

Formula IV wherein,
'$R_4$' is selected from a group comprising H, alkyl, aryl, nitrile, acid and halogen, and wherein the halogen is selected from a group comprising, chloride, fluoride, bromide and iodide;
'$R_5$', '$R_6$', '$R_7$' or '$R_8$' is selected from a group comprising H, OH, alkyl, aryl, halogen, nitro, sulfonates ($SO_3^-$) and nitrile group;
'$R_9$' is selected from a group comprising H and —($CH_2$)$_n$—, wherein 'n' is 1-6; and
'$R_{10}$' is selected from a group comprising hydrogen, —OH, methyl, amine, terminal alkyne, alkene, alkyl acid, amine acid and sulfonates ($SO_3^-$);
'Y' is either Br or I;

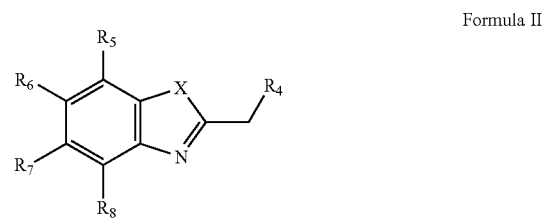

Formula II wherein,
'$R_4$' is selected from a group comprising H, alkyl, aryl, nitrile, acid and halogen, and wherein the halogen is selected from a group comprising, chloride, fluoride, bromide and iodide; and
'$R_5$', '$R_6$', '$R_7$' or '$R_8$' is selected from a group comprising H, OH, alkyl, aryl, halogen, nitro, sulfonates ($SO_3^-$) and nitrile group;

Formula III

Y = Br or I wherein,
'$R_9$' is selected from a group comprising H and —($CH_2$)$_n$—, wherein 'n' is 1-6;
'$R_{10}$' is selected from a group comprising hydrogen, —OH, methyl, amine, terminal alkyne, alkene, alkyl acid, amine acid and sulfonates ($SO_3^-$);

and,
b. reacting the compound of Formula IV with compound of Formula V in presence of piperidine and alcohol,

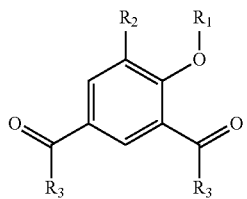

Formula V wherein,
'$R_1$' is hydrogen;
'$R_2$' is selected from a group comprising H, OH, halogen, alkyl and substituted alkyl, and wherein, the halogen is selected from a group comprising bromide, chloride and iodide; and
'$R_3$' is selected from a group comprising H, alkyl, aryl, nitrile, acid and halogen, and wherein the halogen is selected from a group comprising, chloride, fluoride, bromide and iodide.

Thus, the Formula I compounds are synthesized by reacting N-alkylated benzothiazole derivatives with 4-hydroxyisophthalaldehyde derivatives in presence of piperidine. Said synthesis of Formula I compound is shown in Scheme 1 below.

halogen is selected from a group comprising, chloride, fluoride, bromide and iodide;
'$R_5$', '$R_6$', '$R_7$' or '$R_8$' is selected from a group comprising H, OH, alkyl, aryl, halogen, nitro, sulfonates ($SO_3$) and nitrile group;
'$R_9$' is selected from a group comprising H and —$(CH_2)_n$—, wherein 'n' is 1-6;
'$R_{10}$' is selected from a group comprising hydrogen, —OH, methyl, amine, terminal alkyne, alkene, alkyl acid, amine acid and sulfonates ($SO_3^-$).

In a specific embodiment of the present disclosure, the compound of Formula I is quinone cyanine-dithiazole, QCy-DT, and the quinone cyanine-dithiazole, QCy-DT is prepared by:
a. reacting 2-methyl benzothiazole with methyl iodide to obtain N-methyl-2-methylbenzothiazole; and
b. reacting the N-methyl-2-methylbenzothiazole with 4-hydroxyisophthalaldehyde in presence of piperidine Thus, the Formula I compound—QCy-DT is prepared by taking a stirred solution of 2-methyl benzothiazole in dichloromethane, and adding methyl iodide dropwise followed by allowing the reaction to complete which results in a white colored precipitate. The precipitate is filtered and washed to remove the unreacted benzothiazole. To the obtained product (N-methyl-2-methylbenzothiazole) [1] in ethanol, piperidine is added and the solution is allowed to incubate. 4-hydroxyisophthalaldehyde [2] in ethanol is added and the reaction mixture is stirred. After completion of the reaction, the solvent is evaporated and the crude product is purified to obtain the QCy-DT. In an embodiment, scheme 2 depicting the synthesis of QCy-DT is provided below:

Scheme 1: Scheme for the synthesis of compounds of formula 1

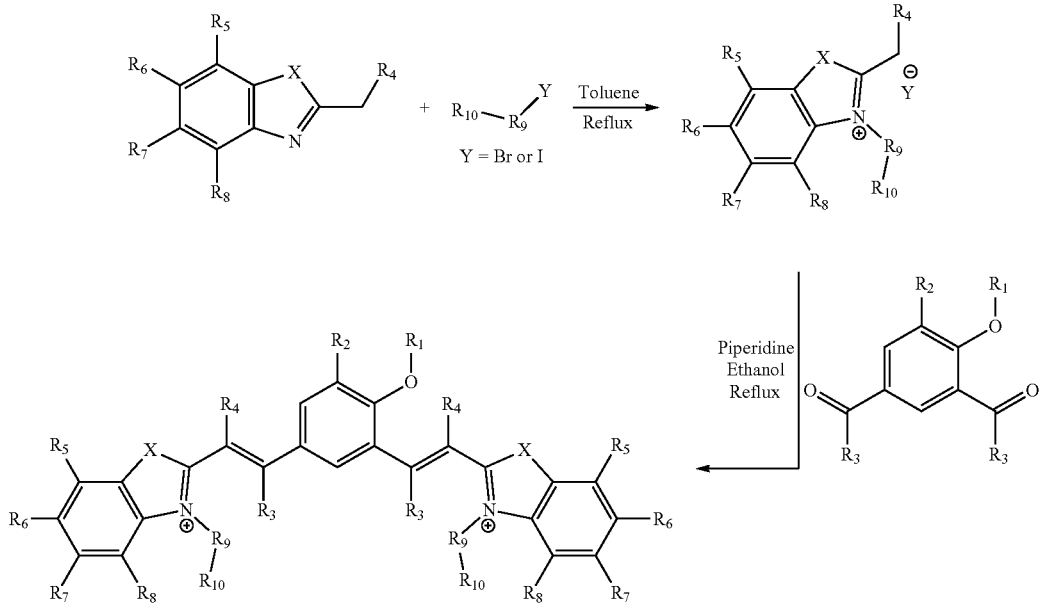

wherein, 'X' is selected from a group comprising oxygen, sulphur, and selenium;
'$R_1$' is hydrogen;
'$R_2$' is selected from a group comprising H, OH, halogen, alkyl and substituted alkyl, and wherein, the halogen is selected from a group comprising bromide, chloride and iodide;
'$R_3$' '$R_4$' is selected from a group comprising H, alkyl, aryl, nitrile, acid and halogen, and wherein the Scheme 2: Scheme for the synthesis of QCy-DT

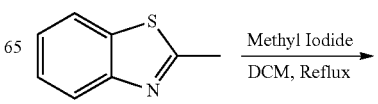

-continued

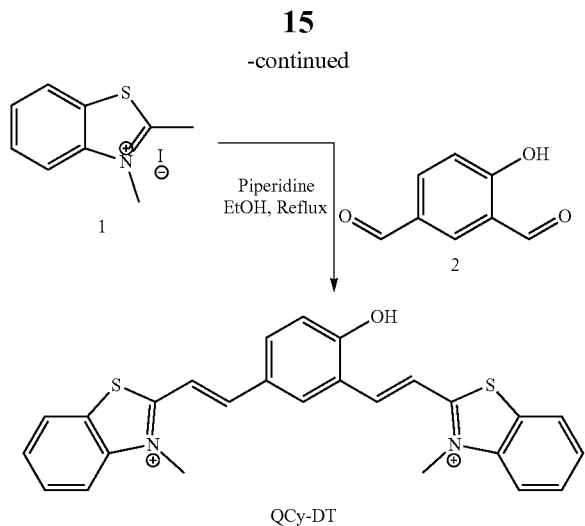

QCy-DT

The processes as described above, wherein said process is carried out at a temperature ranging from about 30° C. to 80° C., and for a time period ranging from about 2 hours to 24 hours.

The process as described above, wherein the steps a) and b) further comprise isolation, purification or a combination thereof of the corresponding product; wherein said isolation and purification is carried out by acts selected from a group comprising addition of solvent, washing with solvent, quenching, filtration, extraction, chromatography and combinations thereof.

The present disclosure also relates to pharmaceutical compositions or formulations comprising one or more compound of Formula I, optionally along with pharmaceutically acceptable excipients. In an embodiment, the pharmaceutically acceptable excipient is selected from a group comprising adjuvant, diluent, carrier, granulating agents, binding agents, lubricating agents, disintegrating agent, sweetening agents, glidant, anti-adherent, anti-static agent, surfactant, anti-oxidant, gum, coating agent, coloring agent, flavouring agent, coating agent, plasticizer, preservative, suspending agent, emulsifying agent, plant cellulosic material, spheronization agent, other conventionally known pharmaceutically acceptable excipient or any combination of excipients thereof. In another embodiment, the pharmaceutical composition of the present disclosure is administered to a subject through modes selected from a group comprising intravenous administration, intramuscular administration, intraperitoneal administration, hepatoportal administration, intra articular administration and pancreatic duodenal artery administration, or any combination thereof.

In an embodiment of the present disclosure, pharmaceutical composition comprises compound selected from

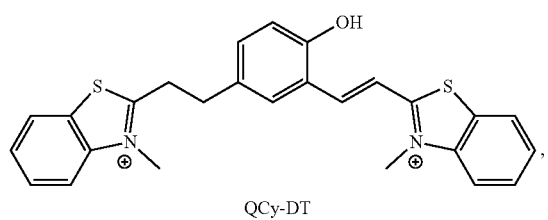

QCy-DT

-continued

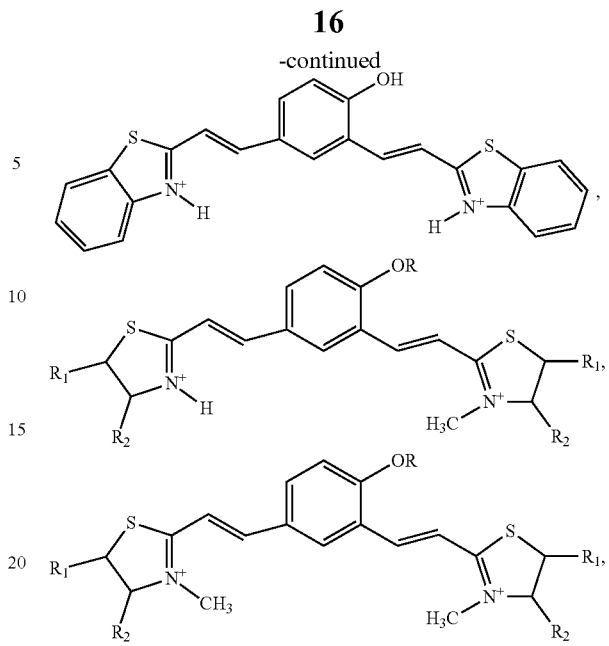

R, $R_1$, $R_2$=any alky aryl or heterocyclic substituents or cyclic structure

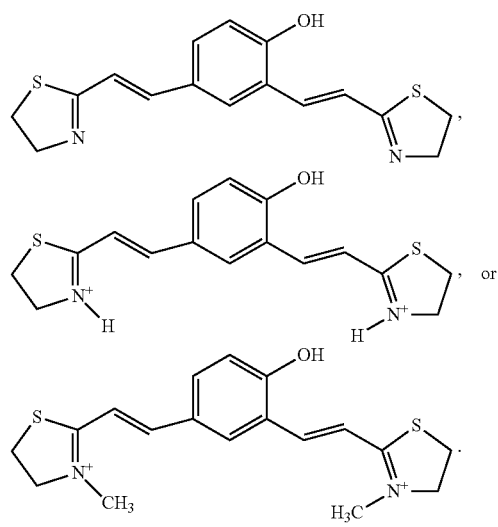

optionally along with said pharmaceutically acceptable excipients.

The present disclosure further provides a method of detection or quantification of DNA sequence, said method comprising:
 a. contacting the probe of compound of Formula I or its derivative, tautomer, isomer, polymorph, solvate or intermediates thereof, or the composition comprising compound of formula I with a DNA or peptide sequence so as to allow for hybridization of the probe with the DNA or peptide sequence; and
 b. detecting or quantifying the binding intensity by measuring the change in fluorescence of the probe resulting from the specific interaction or binding of the probe to DNA or peptide sequence, upon hybridization of the probe to DNA or peptide sequence.

In an embodiment of the present disclosure, the DNA sequence is AT rich sequence.

In another embodiment of the present disclosure, the specific interaction or binding is in the minor groove of DNA, and wherein the compound delocalizes pi electrons between donor acceptor atoms on binding to the DNA minor groove.

In yet another embodiment of the present disclosure, the specific interaction or binding is by base pairing, covalent or non-covalent interaction, resulting in the fluorescence.

In still another embodiment of the present disclosure, the method is for detecting the presence of specific sequences, in particular AT rich sequences in a eukaryotic cell selected from a group comprising cancerous cells, cells infected with microorganisms, unicellular protozoan, parasite and other abnormal cells.

The present disclosure further provides a method for inhibiting growth of a cell, said method comprising contacting the compound of Formula I or its derivative, tautomer, isomer, polymorph, solvate or intermediates thereof, or the composition comprising compound of formula I with the cell. In an embodiment of the present disclosure, the cell is an eukaryotic cell selected from a group comprising cancerous cells, cells infected with microorganisms, parasite or unicellular protozoan and other abnormal cells, and wherein the parasite is *Plasmodium*.

The present disclosure further provides a method of identifying DNA containing AT base pairs, said method comprising contacting the compound of Formula I with a DNA sequence having or suspected of having AT-rich bases.

As used in the present disclosure, the phrase "AT-rich DNA" is a DNA which consists more percentage of AT-base pairs than GC-base pairs. In exemplary embodiments of the present disclosure, AT-rich DNA includes but is not limited to AT-rich region of nuclear DNA such as but not limited to DNA Minor Groove of the double-strand (ds) DNA. In another exemplary embodiment, any DNA with AT base pairs can be detected by employing the compound of Formula I.

In an exemplary embodiment of the present disclosure, the AT-rich DNA sequence is DNA Minor Groove of double-strand (ds) DNA. In another embodiment, the compound of Formula I recognizes the DNA Minor Groove by NIR-Fluorescence Switch-On mechanism. In yet another embodiment, the compound of Formula I identifies AT-rich DNA sequence by NIR-Fluorescence Switch-On mechanism.

In still another embodiment, the compound of Formula I is non-aggregated and non-fluorescent in unbound-state but emits NIR-fluorescence in DNA bound-state, thus resulting in the identification of AT-rich DNA sequence.

The present disclosure also provides a method of staining of cells, said method comprising contacting the compound of Formula I with a cell. In an embodiment, contacting compound of Formula I results in selective staining of nuclear DNA in live or fixed cells. In another embodiment, the compound of Formula I recognizes and binds to the AT-rich regions of the nuclear DNA, particularly the DNA Minor Groove by NIR-Fluorescence Switch-On mechanism. In yet another embodiment, compound of Formula I is non-aggregated and non-fluorescent in unbound-state but emits NIR-fluorescence in DNA bound-state, thus resulting in the staining of DNA.

In some embodiments of the present disclosure, a method of staining unicellular eukaryotic organism is provided wherein said method comprises contacting the compound of Formula I with the organism. In a preferred embodiment, the unicellular eukaryotic organism is a protozoan, preferably, a parasite. In an exemplary embodiment, the parasite is *Plasmodium* species selected from a group comprising but not limiting to *Plasmodium falciparum, Plasmodium vivax, Plasmodium ovale* and *Plasmodium Malariae*. In another embodiment, the compound of Formula I binds to AT-rich regions of the nuclear DNA of *Plasmodium* species, resulting in the staining of *Plasmodium* species.

The present disclosure provides a method of inhibiting the growth of a parasite or any microorganism rich in AT-rich DNA sequence, said method comprising contacting the compound of Formula I with the said parasite or the microorganism. In a specific embodiment, the parasite is *Plasmodium* species selected from a group comprising but not limiting to *Plasmodium falciparum, Plasmodium vivax, Plasmodium ovale*, and *Plasmodium Malariae*. In another specific embodiment, the microorganism rich in AT content is lethal or harmful to mammal, including but not limiting to human being. In an embodiment, the compound of Formula I inhibits the growth of the parasite or the microorganism by targeting nuclear DNA. In another embodiment, uptake of Formula I compound in the nucleus of the parasite or the microorganism abrogates the process of DNA replication resulting in the growth inhibition. In yet another embodiment, the compound of Formula I binds to AT-rich regions of the genome of the parasite or the microorganism resulting in the abrogation of DNA metabolism and subsequent growth inhibition. In an embodiment, the inhibitory concentration ($IC_{50}$) of the compound of Formula I ranges from about 3 µM to 4 µM.

The present disclosure further provides a method for managing or treating a disease or infection in a subject, said method comprising step of administering the compound of Formula I as claimed in claim 1 or any derivative, tautomer, isomer, polymorph, solvate or its intermediates thereof, or the composition comprising compound of formula I in said subject to manage and treat the disease or the infection. In an embodiment, the subject is mammal, preferably human. In another embodiment, the infection is parasitic infection, preferably malaria. In yet another embodiment, the disease is caused due to the presence of cells comprising AT rich DNA, wherein the cell is an eukaryotic cell selected from a group comprising cancerous cells, cells infected with parasite or unicellular protozoan and other abnormal cells. In still another embodiment, the parasitic infection is caused by a parasite selected from a group comprising *Plasmodium falciparum, P. Vivex, P. Malarie* and *P. Ovale*, or any combination thereof.

In an exemplary embodiment, the compound of Formula I is employed for managing or treating disease caused by a microorganism containing AT-rich DNA. In another embodiment, the compound of Formula I is administered to the subject at a concentration ranging from about 0.5 to 1.0 µM.

As used herein, "management" or "managing" refers to preventing a disease or disorder from occurring in a subject, decreasing the risk of death due to a disease or disorder, delaying the onset of a disease or disorder, inhibiting the progression of a disease or disorder, partial or complete cure of a disease or disorder and/or adverse effect attributable to the said disease or disorder, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder and/or adverse effect attributable to the disease or disorder), relieving a disease or disorder (i.e. causing regression of the disease or disorder). Further, the present disclosure envisages managing/treating said disease/disorder/infection by administering therapeutically effective dosage of Formula I compound(s) or composition/formulation thereof of the invention.

The present disclosure also relates to the use of Formula I compounds for in-vitro and in-vivo identification of AT-rich DNA, cell imaging/cell staining, use in inhibiting growth of parasites and use in the treatment of parasitic infections/disease/disorder.

The present disclosure also relates to the use of compound of Formula I or any derivative, tautomeric form, isomer, polymorph, solvate and intermediates thereof, or the composition comprising compound of formula I for detecting or quantifying the presence of specific DNA or peptide sequence, in particular AT-rich DNA sequence, inhibiting growth of cells or a combination thereof, and for in-vitro and in-vivo cell imaging.

The present disclosure also relates to the use of compound of Formula I as claimed in claim 1 or any derivative, tautomer, isomer, polymorph, solvate or its intermediates thereof, or the composition comprising compound of formula I in the manufacture of a medicament for treatment of parasitic infection or in the manufacture of stimuli responsive probes.

The present disclosure also relates to the use of compound of Formula I as claimed in claim 1 or any derivative, tautomer, isomer, polymorph, solvate or its intermediates thereof, or the composition comprising compound of formula I in the manufacture of stimuli responsive probes.

The present disclosure also relates to a method of diagnosing disease characterized by presence of specific DNA or peptide sequence or abnormal levels of AT rich DNA, the method comprising:
a. contacting the probe of compound of Formula I with a biological sample comprising DNA or peptide sequence to allow for hybridization of the probe with the DNA or peptide sequence or antibodies;
b. removing the unhybridized probe from the mixture; and
c. detecting or quantifying the presence of specific DNA or peptide sequence, by measuring the change in fluorescence of the probe resulting from the specific interaction or binding of the probe to DNA, upon hybridization of the probe to DNA to diagnose the disease.

Additional embodiments and features of the present disclosure will be apparent to one of ordinary skill in art based upon description provided herein. However, the examples and the figures should not be construed to limit the scope of the present disclosure.

EXAMPLES

Material and Methods

All the chemicals, reagents, single-stranded oligos ($dA_{20}$, $dT_{20}$, $dG_{20}$, $dC_{20}$), self-complementary oligos {$d(ATAT)_5$, $(D1)_{mix}$, Drew-AT, Calf-Thymus DNA (CT-DNA), (DM1, DM2, DM3, DM4, DM5, DM6 and DM7)}, RNA, were purchased from Sigma-Aldrich. $^1$H and $^{13}$C NMR spectra were recorded on a Bruker AV-400 MHz spectrometer with chemical shifts reported as parts per million (ppm) (in DMSO-d6, tetramethylsilane as an internal standard) at 20° C. UV-vis absorption and emission spectra were measured in quartz cuvettes of 1 cm path length. High resolution mass spectra (HRMS) were obtained on Agilent Technologies 6538 UHD Accurate-Mass Q-TOF LC/MS spectrometer. All biophysical studies (UV-vis, fluorescence and Cirular dichroism) are carried out at the concentration 0-5 µM of probe, volume=500 µL, temperature=25° C. and time of incubation=2 minutes. HeLa cells and MCF7 cells used in the biological studies are obtained from "Molecular reproduction, development and genetics lab, Indian institute of science, Bangalore, India"

Example 1

Synthesis of QCy-DT

To a stirred solution of 2-methyl benzothiazole (7.0 mmol) in dichloromethane (10 mL), methyl iodide (14.0 mmol) is added dropwise and allowed to reflux overnight. Completion of the reaction is monitored by thin layer chromatography (TLC). After completion of the reaction, a white colored precipitate is formed. The precipitate is filtered and washed with copious amount of diethyl ether for removing the unreacted benzothiazole. The obtained product (N-methyl-2-methylbenzothiazole) (1) is dried under vacuum and used for the next reaction without further purification.

Piperidine (8 µL) is added to a stirred solution of N-methyl-2-methylbenzothiazole (1) (0.1 g, 0.34 mmol) in ethanol (8 mL). After about 10 min, 4-hydroxyisophthalaldehyde (2) (20 mg, 0.14 mmol) in ethanol (2 mL) was added and the reaction mixture is stirred at about 80° C. for about 3 hours under nitrogen atmosphere. After completion of reaction, solvent is evaporated and the crude product is purified by preparative RP-HPLC (grad. 50-65% acetonitrile in water, about 12 min) to obtain the probe QCy-DT as a yellow powder.

Yield 45%. IR (neat): 3390, 3065, 3015, 1682, 1667, 1582, 1505, 1121 cm$^1$, $^1$H NMR (400 MHz, DMSO-d$_6$) $\delta_{ppm}$: 8.59 (d, J=2 Hz, 1H), 8.42 (d, J=8.1 Hz, 2H), 8.30 (d, J=8.2 Hz, 1H), 8.26 (d, J=3.3 Hz, 1H), 8.23 (d, J=10.7 Hz, 1H), 8.19 (dd, J=2 Hz, J=8.7 Hz, 1H), 8.13 (dd, J=8.1 Hz, J=16 Hz, 2H), 7.98-7.89 (m, 3H), 7.86 (dd, J=1.1 Hz, J=9.5 Hz, 1H), 7.83-7.78 (m, 2H), 7.22 (d, J=8.7 Hz, 1H), 4.36 (s, 6H). $^{13}$C NMR (100 MHz, DMSO-d$_6$) $\delta_{ppm}$: 172.1, 171.8, 161.8, 147.7, 142.2, 142.1, 142.0, 134.8, 132.6, 129.5, 128.5, 127.8, 127.6, 125.9, 124.1, 121.5, 117.7, 116.9, 116.8, 114.3, 111.8, 36.3, 36.2. HRMS (ESI-MS): found 441.1070, calcd. for $C_{26}H_{22}N_2OS_2$ [M-2I-H]$^{1+}$ m/z=441.1095 (FIGS. 23 and 24)

Example 2

Photophysical Properties of QCy-DT

Sample Preparation for UV-Vis and Fluorescence Measurements

Stock solutions of QCy-DT are prepared in double-distilled (dd) water in the order of 10$^{-3}$ M and stored at about −10° C. DNA stock solutions are prepared by dissolving oligo samples in double-distilled (dd) water in the order of 10$^{-4}$ M. Solutions of DNA duplexes are prepared in Tris-HCl (100 mM, pH=7.4) buffer solution by mixing complementary DNA strands in equimolar concentration. This solution is then subjected to annealing by heating up to about 85° C. for about 15 minutes, subsequently cooled to room temperature for about 7 hours and stored in the refrigerator (about 4° C.) for about 4 hours.

Absorption and Emission Spectra

The UV-vis absorption and emission spectra are recorded on Agilent Technologies Cary series UV-vis-NIR absorbance and Cary eclipse fluorescence spectrophotometers, respectively. Thermal denaturation (UV-melting) studies are carried out on Cary 5000 UV-vis-NIR spectrophotometer equipped with Cary temperature controller in the range of 10° C. to 90° C. with a ramp rate of 1° C./min. The variable temperature/wavelength mode is used. Absorption is monitored at 260 nm with regular 5° C. intervals. Melting temperatures ($T_m$) of DNA samples are calculated from the first derivatives of the absorption vs. temperature curves (thermal denaturation or melting curves) obtained by monitoring at 260 nm.

Figure 1A:
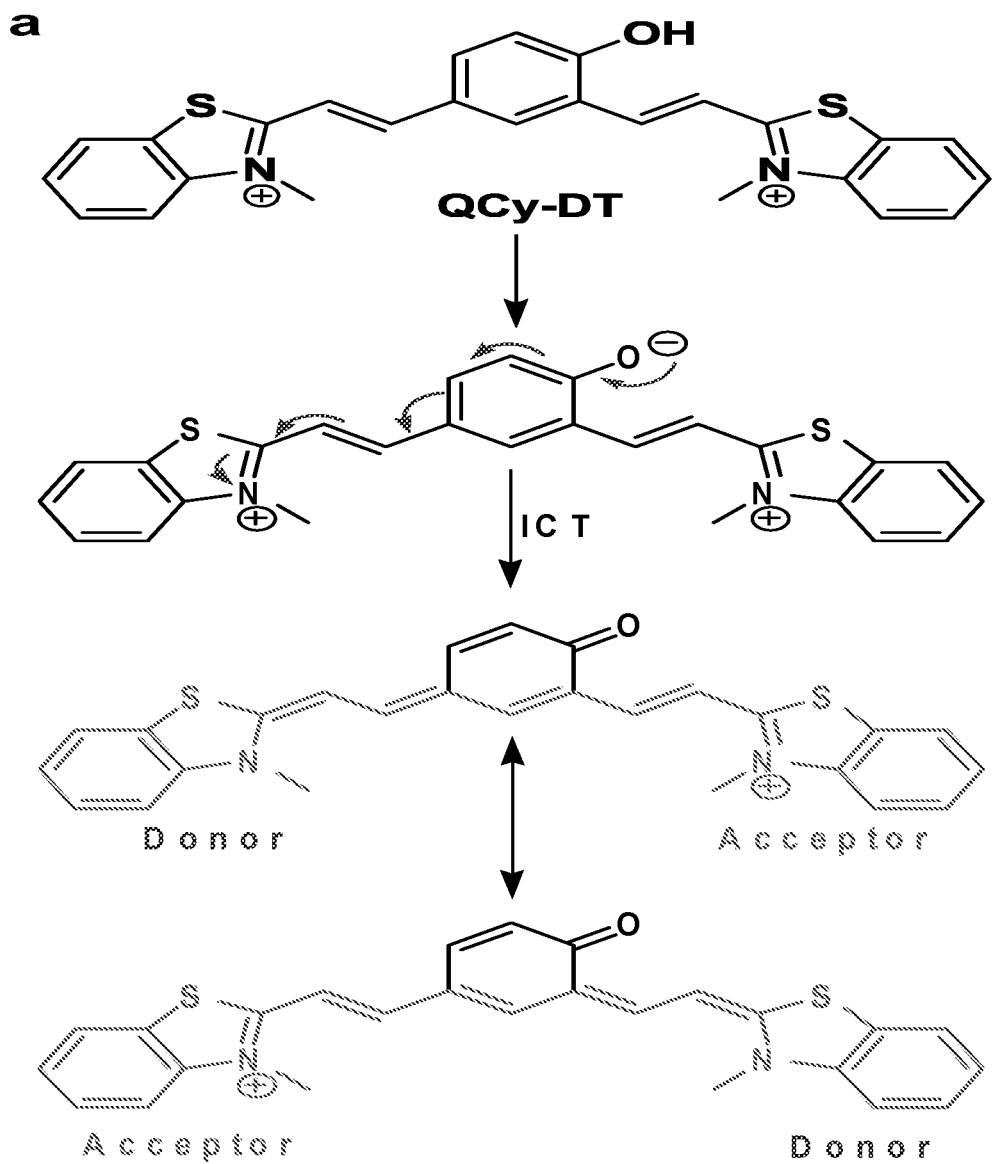

Results:

As illustrated in FIG. 1, deprotonation of phenol generates phenolate, which donates electrons to one of the conjugated acceptors (N-alkylated benzothiazole) and triggers internal charge transfer (ICT) to the quaternary nitrogen atom on another benzothiazole group. This ICT process results in the generation of a highly delocalized π-electron system, resembling the Cy7 fluorophore (FIG. 1*a*). However, the protonated form of QCy-DT (i.e., phenol form) is non-fluorescent due to the lack of the ICT process. In order to assess the conditions for deprotonation of QCy-DT to generate phenolate, pH-dependent fluorescence measurements is performed in Tris-HCl solution (100 mM, pH=7.4). Under acidic conditions (pH=2-5), QCy-DT did not fluoresce, owing to a stable phenol form. Interestingly, the probe showed weak but basal NIR-fluorescence ($\lambda_{max}$=680 nm) in the pH range of 6-8 (FIG. 8). Thus, pH-dependent fluorescence study revealed that under physiological conditions, QCy-DT exists mostly in the phenolate form with basal NIR-fluorescence (NIR-ready). The weak but basal fluorescent nature of QCy-DT (NIR-ready fluorescence probe) under physiological conditions meets the primary criterion that the probe is relatively non-fluorescent in the unbound-state but fluoresces strongly in DNA bound-state.

Figure 1B:
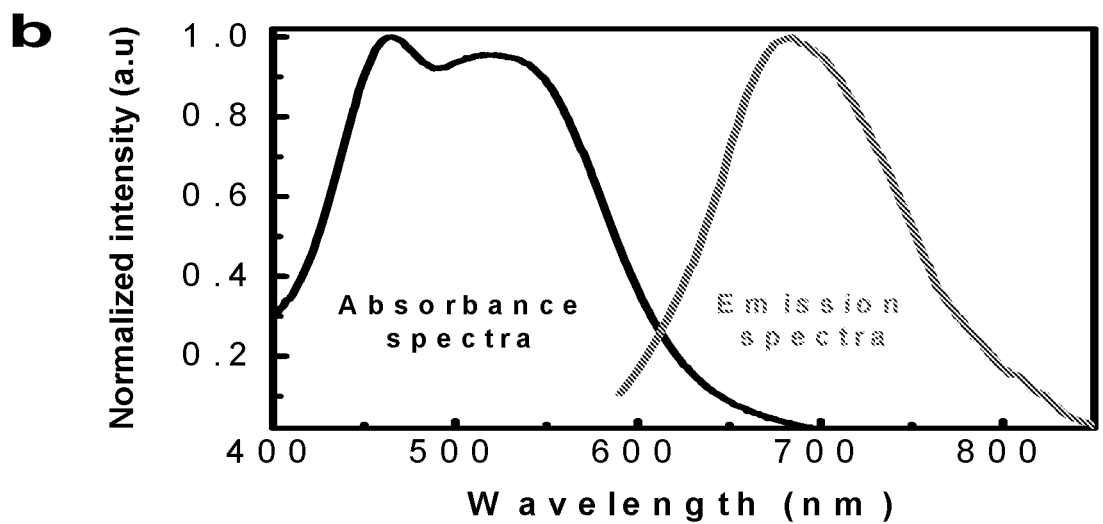

The molecular interactions of QCy-DT is studied by evaluating the absorption and emission properties in Tris-buffer (100 mM, pH=7.4) under ambient conditions. The UV-vis absorption spectra of QCy-DT (2 µM) exhibit two absorption maxima at 463 and 530 nm (FIG. 1*b*) ($\varepsilon$=14,950 $M^{-1}$ $cm^{-1}$). The absorption band at 530 nm originates from the delocalization of π-electrons between phenolic oxygen and p-substituted benzothiazolium vinyl moiety in QCy-DT while the band at 463 nm is from the similar conjugation of o-substituted benzothiazolium vinyl moiety in QCy-DT. The absorption spectra of QCy-DT showed a linear increase in absorbance with increasing concentration from 0 to 8 µM (FIG. 9). This linear increase in absorbance in the range of 0 to 8 µM of QCy-DT suggests molecularly dissolved and non-aggregated state in buffer solution, under ambient conditions. Upon excitation at 530 nm, QCy-DT showed a weak but basal emission peak in the NIR region at 680 nm with a large Stokes shift ($\Delta\lambda_{max}$=–150 nm) (FIG. 1*b*). This is a very useful property as it helps avoid self-absorption in the higher energy part of emission. Furthermore, the large Stokes shift of QCy-DT makes it superior to many of the known DNA-binding cyanine probes such as TO, YO, Picogreen, SYBR-Green I, cyanine dimers TOTO-1 and YOYO-1 (Table 1). The NIR-fluorescence of QCy-DT arises due to extended through the Cy7 backbone and ICT process. The weak or non-fluorescent behavior of dye molecules in buffer solution is mainly attributed to the intramolecular twisting processes, which cause quenching of the fluorescence of cyanine dyes, solvation with water molecules also aids the fluorescence quenching by means of deactivation of radiative pathways. We believe both these processes contribute to the weak or non-fluorescent nature of QCy-DT in buffer solution.

TABLE 1

Stokes shift values of cyanine dyes in presence and absence of DNA

| Cyanine Dye | In absence of DNA (nm) | In presence of DNA (nm) |
|---|---|---|
| Thiazole orange (TO) [a] | 139 | 18 |
| Oxazole yellow (YO) [a] | 100 | 19 |
| TOTO-1 [a] | 149 | 19 |
| YOYO-1 [a] | 106 | 20 |
| Picogreen [b] | 30 | 21 |
| SYBR Green 1 [b] | 36 | 26 |
| QCy-DT [c] | 150 | 86 |

[a] Rye, H.S., Yue, S., Wemmer, D.E., Quesada, M.A., Haugland, R.P., Mathies, R.A. and Glazer, A.N. (1992) Stable fluorescent complexes of double-stranded DNA with bis-intercalating asymmetric cyanine dyes: properties and applications. *Nucleic Acids Res.*, 2803-2812.
[b] Cosa, G., Focsaneanu, K.-S., McLean, J. R.N., McNamee, J.P. and Scaiano, J.C. (2001) Photophysical properties of fluorescent DNA-dyes bound to single-and double-stranded DNA in aqueous buffered solution. *Photochem. Photobiol.*, 585-599.
[c] Present disclosure.

Next, the ground-state and excited-state calculations are performed using Density Functional Theory (DFT) with the PBE0 functional and 6-311++G(d,p) basis set for all atoms to support our assignments of the absorption and emission bands of QCy-DT in water. DFT calculations show that the two π-π* transitions are located near 2.32 eV (S1) and 2.88 eV are in good agreement with two experimentally observed absorption bands of QCy-DT in buffer solution, as shown in FIG. 1*b*. The first π-π* state is the lowest transition dominated by the HOMO to LUMO (97%) configuration while the second π-π* state is dominated by the configuration HOMO to LUMO+1 (97%). Relevant molecular orbitals for these transitions are shown in FIG. 10.

Example 3

Switch-on NIR-Fluorescence in the Presence of DNA

Figure 1C:
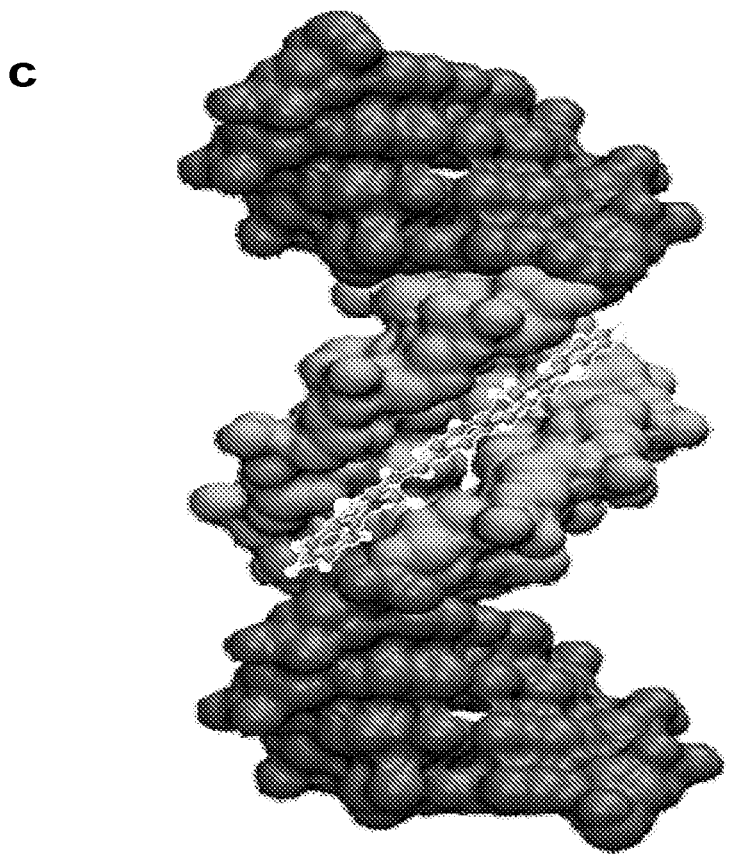
Figure 2:
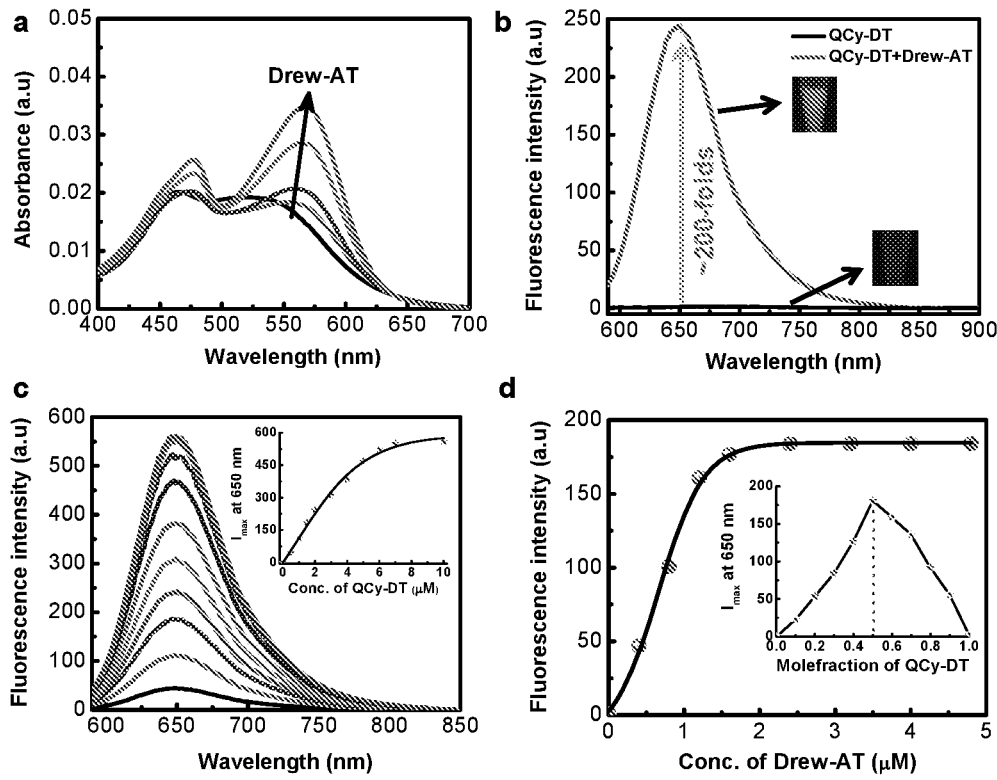

The large Stokes shift, molecularly dissolved-state and non-fluorescent behavior of QCy-DT in buffer solution resulted in the assessment of its recognition ability of DNA. For this, poly AT-duplexes such as $(A-T)_{20}$, self-complementary $d(ATAT)_5$, Drew-AT (14 base pair self-complementary sequence with 6AT-base pairs in central core), poly GC-duplex $(G-C)_{20}$, $(D1)_{mix}$, which is a 16 base pair long self-complementary duplex and CT-DNA as mixed AT/GC duplexes is chosen (Table 2). In the presence of Drew-AT, QCy-DT (2 µM) showed prominent red-shifted ($\Delta\lambda_{max}$=–34 nm) absorption spectrum with good hyperchromicity in the absorption intensity. Upon sequential addition of Drew-AT (0, 1, 2, 3 and 4 µM), the absorption spectra of QCy-DT showed a gradual red shift in the absorption maxima (463 to 479 nm and 530 to 564 nm) with hyperchromicity (FIG. 2*a*). QCy-DT experience hydrophobic environment upon binding to minor groove of AT-rich duplex DNA which prevents aromatic π-stacking interactions with base pairs and other molecules of the probe that led to the hyperchromicity in the absorbance maximum of QCy-DT. Remarkably, QCy-DT showed a ~200-fold enhancement in the fluorescence emission at $\lambda_{em}$=650 nm in the presence of Drew-AT with blue shift ($\Delta\lambda_{max}$=~27 nm) compared to basal fluorescence of the probe alone (FIG. 2*b*). Further, the absorption and emission properties of QCy-DT in the presence of poly AT- and GC-duplexes are studied. In the presence of $(A-T)_{20}$, QCy-DT showed red shift in the absorption maxima with hyperchromicity similar to that of Drew-AT (FIG. 11*a*). QCy-DT exhibited only a slight red shift in the absorption maxima at 463 and 530 nm in the presence of $(G-C)_{20}$, $(D1)_{mix}$ and d(ATAT)$_5$ (FIG. 11b-d). Interestingly, QCy-DT showed almost ~250-fold fluorescence enhancement for (A-T)$_{20}$, compared to the only 8-fold increase observed for (G-C)$_{20}$ duplex (FIG. 12a). Further, we also studied the emission behavior of QCy-DT in presence of CT-DNA, (D1)$_{mix}$, single-stranded (ss) DNAs and RNA. In CT-DNA, (D1)$_{mix}$ and ssDNAs exhibited ~40, ~55 and ~2-fold enhancements, respectively. Fluorescence spectra showed a very weak response of QCy-DT in presence of RNA that confirmed selectivity of the probe for DNA duplexes containing AT-base pairs (FIG. 12b). To ascertain the switch-on behavior of QCy-DT in the presence of AT-rich DNA duplex, viscosity measurements are performed by increasing the glycerol content in buffer solution. With increasing glycerol content, fluorescence spectra of QCy-DT exhibited a gradual enhancement in the emission intensity at 680 nm (FIG. 13). This tendency of the probe to have increased emission intensity with an increase in the glycerol content clearly suggests that the restriction of intramolecular rotation is responsible for the fluorescence enhancement of QCy-DT. Consequently, the observed strong fluorescence enhancement in the presence of AT-rich DNA duplexes is the result of restriction of intramolecular rotation of probe QCy-DT in the constrained environments of DNA, which also facilitates the desolvation (water molecules) around QCy-DT in the hydrophobic environment of DNA duplex (FIG. 1c). These results, thus, confirms switch-on NIR-fluorescence behavior of QCy-DT in the presence of AT-rich DNA duplexes compared to that of GC-rich DNA duplex, ssDNAs and RNA.

TABLE 2

DNA used in this study (with sequence information)

| Code | DNA duplex | Sequence |
|---|---|---|
| Drew AT | mixed DNA | 5'-GCGCAAATTTGCGC-3' <br> 3'-CGCGTTTAAACGCG-5' |
| (A-T)$_{20}$ | dA$_{20}$-dT$_{20}$ | 5'-AAAAAAAAAAAAAAAAAAAA-3' <br> 3'-TTTTTTTTTTTTTTTTTTTT-5' |
| D(ATAT)$_5$ | d(ATAT)$_5$ | 5'-ATATATATATATATATATAT-3' <br> 3'-TATATATATATATATATATA-5' |
| (G-C)$_{20}$ | dG$_{20}$-dC$_{20}$ | 5'-GGGGGGGGGGGGGGGGGGGG-3' <br> 3'-CCCCCCCCCCCCCCCCCCCC-5' |
| (D1)mix | mixed DNA | 5'-CGATAAGCGCTTATCG-3' <br> 3'-GCTATTCGCGAATAGC-5' |
| CT-DNA | mixed DNA | — |

Example 3

Figure 3:
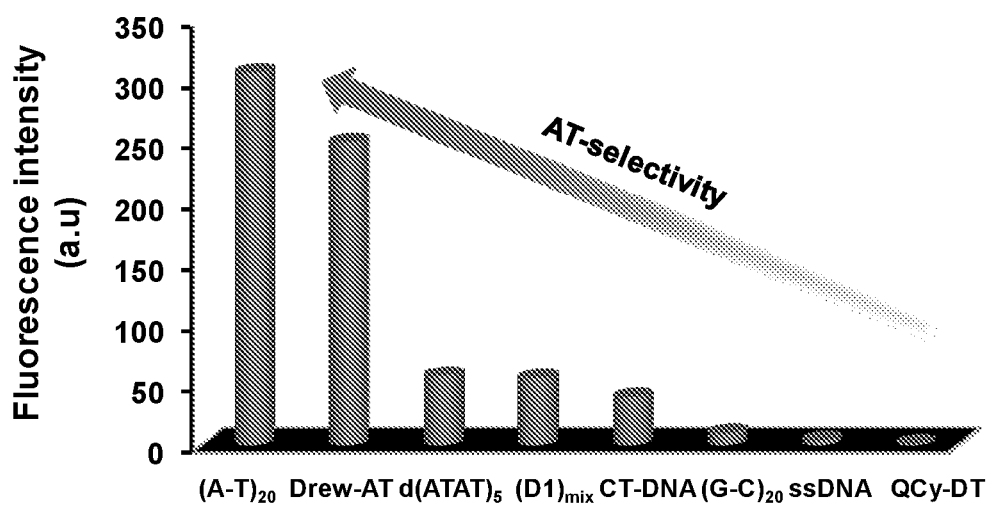
FIG. 3 depicts base pair-dependent recognition of AT-rich DNA by QCy-DT.

Base Pair-Specific Recognition and Switch-on Fluorescence in the Presence of DNA To gain deeper insights into base pair selectivity of the probe, comparative and base pair-dependent fluorescence measurement is performed in the presence of (A-T)$_{20}$, d(ATAT)$_5$, Drew-AT, (D1)$_{mix}$ and (G-C)$_{20}$ duplexes with 20, 6, 4 and 0 sets of AT-base pairs, respectively. We observed ~8, ~55, ~54, ~200 and ~250-folds fluorescence enhancement in the presence of (G-C)$_{20}$, (D)$_{mix}$, d(ATAT)$_5$, Drew-AT and (A-T)$_{20}$ with increasing number of AT-base pairs, respectively (FIG. 3). Further, concentration-dependent studies are carried out with (A-T)$_{20}$ and Drew-AT duplexes by adding increasing concentrations of QCy-DT. With increasing concentration of QCy-DT (0-8 µM) to (A-T)$_{20}$ duplex, the fluorescence intensity gradually increased at 650 nm and attained saturation at ≥6 µM (FIG. 14). Similar spectral changes are observed for QCy-DT in the presence of Drew-AT (FIG. 2c). The fluorescence spectra of QCy-DT is also recorded with increasing concentrations of (A-T)$_{20}$, Drew-AT, d(ATAT)$_5$ and (D1)$_{mix}$ duplexes. FIG. 2d shows a gradual increase in fluorescence with increasing concentration of Drew-AT from 0 to 2 µM and saturation ≥2 M. Upon increasing concentration of other duplexes (A-T)$_{20}$, d(ATAT)$_5$ and (D1)$_{mix}$ QCy-DT showed similar fluorescence enhancement (FIG. 15). Overall, the strong fluorescence enhancements proves QCy-DT to be a selective and NIR-fluorescence-ready probe for DNA containing AT-base pairs (FIG. 3).

Example 4

Binding Stoichiometry, Affinity and Quantum Yield of QCy-DT for DNA Duplexes

To determine the binding stoichiometry of QCy-DT with Drew-AT, continuous variation method is employed, varying the ligand concentrations to generate the Job plot by fixing the total concentration of [QCy-DT+Drew-AT] at 2 µM. The Job plot analysis showed maximum fluorescence at 0.5, indicating 1:1 binding stoichiometry for the [QCy-DT: Drew-AT]complex (FIG. 2d, Inset). The binding constants of [QCy-DT+DNA] complexes are calculated from the fluorescence titration experiments using non-linear (single-binding mode) curve fitting analysis. QCy-DT showed the maximum binding affinity ($K_a$=2.9×10$^6$ M$^{-1}$) for (A-T)$_{20}$, which is 2-folds higher than that for Drew-AT ($K_a$=1.5×10$^6$ M$^{-1}$). The mixed sequence (D1)$_{mix}$ showed relatively weaker binding affinity ($K_a$=4.3×10$^5$ M$^{-1}$) compared to AT-rich DNA duplexes (FIG. 16). Next, the fluorescence quantum yield of QCy-DT is estimated in the presence of AT- and GC-rich DNA duplexes (Table 3) as follows:

Quantum Yield Calculation

Cresyl violet perchlorate in ethanol (φ=0.54) is used as the standard for the fluorescence quantum yield calculation using the absorption of the test sample. The emission spectral area is obtained in the 550-800 nm regions. Dilute solutions (10$^{-6}$ M) are used to minimize reabsorption effects of the dyes. Quantum yields are determined using the following equation, $$\phi_s = \phi_r (F_s/F_r) \times (A_r/A_s) \times (n_s^2/n_r^2)$$

Where, $\phi_r$ and $\phi_s$ are the quantum yield of reference and sample respectively, $F_r$ and $F_s$ are the integrated intensities (areas) of standard and sample spectra, nr and ns are the refractive indices of the reference and sample solution, $A_r$ and $A_s$ are the absorbance intensities of reference and sample respectively.

TABLE 3

The fluorescence quantum yields of probe QCy-DT in the absence and presence of DNA

| QCy-DT | Quantum Yield ($\Phi_F$) |
|---|---|
| Tris-HCl | 0.0039 |
| Glycerol | 0.07 |
| (A-T)$_{20}$ | 0.32 |

TABLE 3-continued

The fluorescence quantum yields of probe QCy-DT in the absence and presence of DNA

| QCy-DT | Quantum Yield ($\Phi_F$) |
|---|---|
| Drew-AT | 0.25 |
| D(ATAT)$_5$ | 0.08 |
| (D1)$_{mix}$ | 0.08 |

$\Phi_F$: Fluorescence quantum yields are measured using Cresol Violet in ethanol as reference. Experimental conditions: Tris-HCl buffer (100 mM, pH = 7.4). Molar absorption coefficient for QCy-DT: 14,950 M$^{-1}$ cm$^{-1}$ QCy-DT alone showed very low fluorescence quantum yield ($\Phi_F$=~0.004) and increased significantly in the presence of glycerol ($\Phi_F$=~0.07). Remarkably, QCy-DT showed maximum fluorescence quantum yield in the presence of (A-T)$_{20}$ ($\Phi_F$=~0.32) and Drew-AT ($\Phi_F$=~0.25) compared to other duplexes used in the present study (Table 2). To understand the effect of QCy-DT binding to DNA on the thermal stability of DNA, temperature-dependent UV-melting studies (UV-T$_m$) is performed on different [QCy-DT+DNA] complexes. The UV-T, studies of QCy-DT-bound (A-T)$_{20}$, Drew-AT, d(ATAT)$_5$ and (D1)$_{mix}$ showed increase in melting temperatures (T$_m$) with $\Delta T_m$=6.2, 4.2, 3.5 and 2.5° C., respectively (Table 4). The T$_m$ data showed moderate stabilization of DNA duplexes in the presence of QCy-DT. Therefore, the binding affinity, fluorescence quantum yield, and UV-T$_m$ data validated the preferential recognition of AT-rich DNA by QCy-DT probe compared to GC-rich DNA.

TABLE 4

Difference in melting temperatures ($\Delta T_m$) of DNA duplex and in presence of QCy-DT

| DNA-Duplex | $\Delta$Tm (° C.) |
|---|---|
| (A-T)$_{20}$ | 6.2 |
| Drew AT | 4.2 |
| d(ATAT)$_5$ | 3.5 |
| (D1)$_{mix}$ | 2.5 |

Example 5

Mode of AT-rich DNA Recognition by QCy-DT
Circular Dichroism (CD) Spectroscopy

To determine the binding mode of QCy-DT to AT-rich (A-T)$_{20}$ and Drew-AT DNA duplexes, circular dichroism (CD) studies are carried out under ambient conditions. CD measurements are carried out on Jasco J-815 spectrometer equipped with a Peltier-type temperature controller (CDF-4265/15) under a nitrogen atmosphere to avoid water condensation. Scans are performed over the range of 200-700 nm with a speed of 100 nm/min, and the spectra represent an average of three scans. A blank sample containing Tris-HCl buffer solution (100 mM, pH=7.4) is treated in the same manner and subtracted from the collected data.

Figure 4:
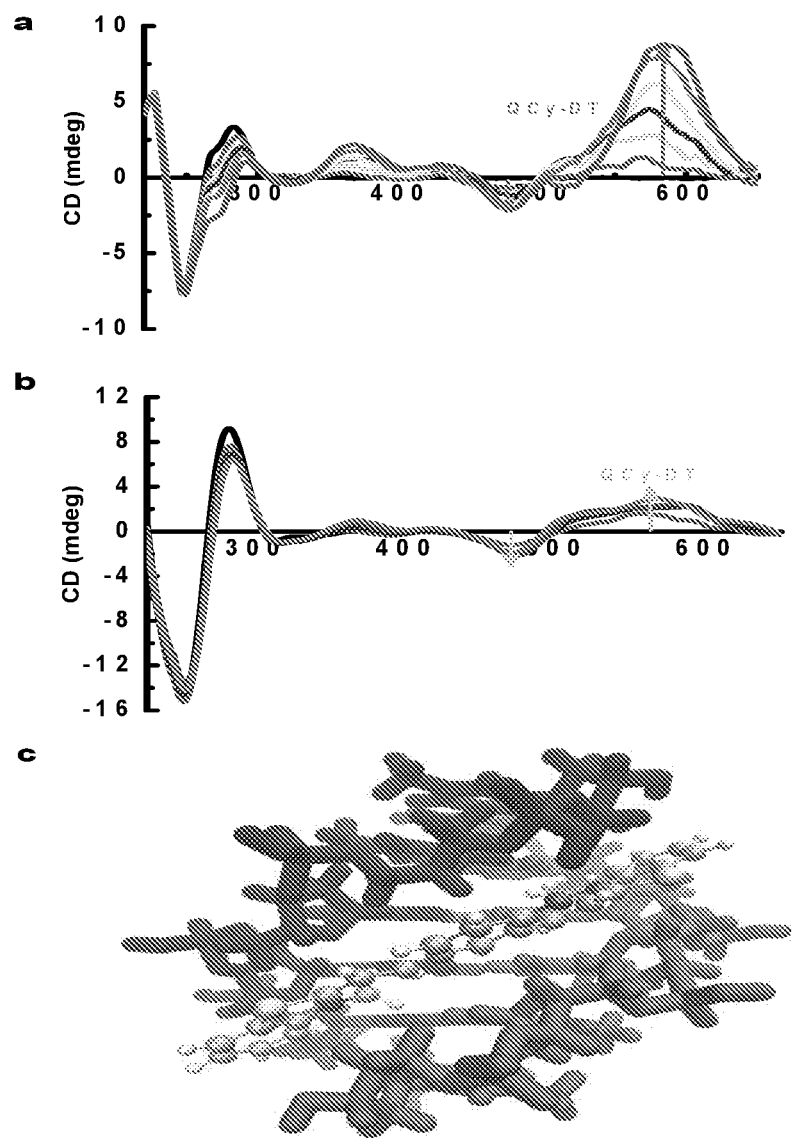
FIG. 4 depicts circular dichroism (CD) spectra of QCy-DT in the presence of AT-rich DNA duplexes and view of minor groove binding mode of QCy-DT. (a) & (b) CD spectra of $(A-T)_{20}$ (4 µM) and Drew-AT (4 µM) with increasing concentration of QCy-DT from 0 to 16 µM respectively. (c) Geometry optimized structure of the AT-rich DNA complexed with QCy-DT in the minor groove.

CD spectrum of (A-T)$_{20}$ alone showed a positive and a negative signal at 280 and 248 nm, respectively. Similarly, Drew-AT showed a positive and a negative signal at 280 and 250 nm, respectively. These characteristic positive and negative CD signals confirm the typical B-form DNA duplex structure. At this point, two binding modes intercalation and minor groove binding are expected for QCy-DT binding to DNA. From the CD data, these modes can be distinguished by means of induced CD signal for the guest (probe) to confirm groove binding over intercalation. Accordingly, interactions between QCy-DT and DNA could be monitored by induced CD signals in the >300 nm region that gives information about the chiral environment around the probe on DNA. The concentration-dependent CD spectra recorded by the addition of increased concentrations of QCy-DT (2-16 μM) to fixed concentration of (A-T)$_{20}$ (4 μM) showed strong induced positive CD signals at 575 and 366 nm and a negative signal at 476 nm in the absorption regions of QCy-DT (FIG. 4a). Similarly, we observed induced CD signals for QCy-DT in the presence of Drew-AT, though with relatively low intensity (FIG. 4b). Thus, characteristic induced CD signal in the QCy-DT absorption region revealed that the probe bound to the minor groove of AT-rich DNA duplexes.

Furthermore, ab initio theoretical calculations to unravel various features of QCy-DT/DNA interaction is performed using density functional theory (DFT) methods. Two possible modes (intercalation and groove binding) are considered for the binding of the bent QCy-DT to duplex DNA. The DNA phosphate backbone is neutralized by adding hydrogen to one of the oxygen atoms of the phosphate groups that would not alter any property of the duplex DNA structure. To calculate the binding energies of QCy-DT with DNA, AT- and GC-rich duplexes (A/T and G/C) is chosen for each of these modes (Table 5). The computed binding energy values confirm that QCy-DT prefers to bind in the minor groove of duplex DNA irrespective of the sequences. An inspection of the binding energy table reveals that the probe binds more strongly to AT-base pair (−105 to −110 kcal/mol) compared to GC-base pair (−85 to −90 kcal/mol) containing duplexes. Thus, QCy-DT is found to be better accommodating in the minor groove of AT-rich DNA than GC-rich ones, which is apparent from the binding energy values (FIG. 4c). Generally, the floor of minor groove with AT-base pairs has the highest negative electrostatic potentials while GC-base pairs possess the highest positive potentials. Naturally, the positively charged QCy-DT prefers to bind in the AT-rich minor grooves of DNA compared to minor groove consisting of GC-base pairs. In the present calculations, two possible orientations of QCy-DT in the minor groove of AT-base pair containing DNA is considered, and the cationic quaternary nitrogen centres of the molecule can be located either (i) inside or (ii) outside of the groove. In this respect, binding energy values suggest that the former orientation where the cationic centres arranged inside the minor groove of DNA are stabilized by −35 kcal/mol more than the latter. Snapshots of the optimization process of 5'-AAATTT-3'/QCy-DT complex are shown in FIG. 17. Overall, computational results are well-corroborated with the experimental data that QCy-DT prefers to bind in the minor groove, with a preference for AT-base pairs over GC-base pair containing DNA.

TABLE 5

Binding mode and binding energies of QCy-DT in presence of AT-rich and GC-rich DNA duplexes

| DNA-Duplex | Binding mode | Binding energy (kcal/mol) |
|---|---|---|
| 5'-AAATTT-3' | Minor | −105.51 |
| 3'-TTTAAA-5' | major | −45.08 |
| | intercalation | −65.38 |

TABLE 5-continued

Binding mode and binding energies of QCy-DT in presence of AT-rich and GC-rich DNA duplexes

| DNA-Duplex | Binding mode | Binding energy (kcal/mol) |
|---|---|---|
| 5'-AAAAAA-3'<br>3'-TTTTTT-5' | Minor<br>major<br>intercalation | -108.48<br>-62.26<br>-60.29 |
| 5'-GCGCGC-3'<br>3'-CGCGCG-5' | Minor<br>major<br>intercalation | -85.34<br>-54.01<br>-60.50 |
| 5'-GGGGGG-3'<br>3'-CCCCCC-5' | Minor<br>major<br>intercalation | -91.01<br>-86.56<br>-61.39 |

Example 6

Sequence-Specific Recognition of DNA by QCy-DT

Figure 5:
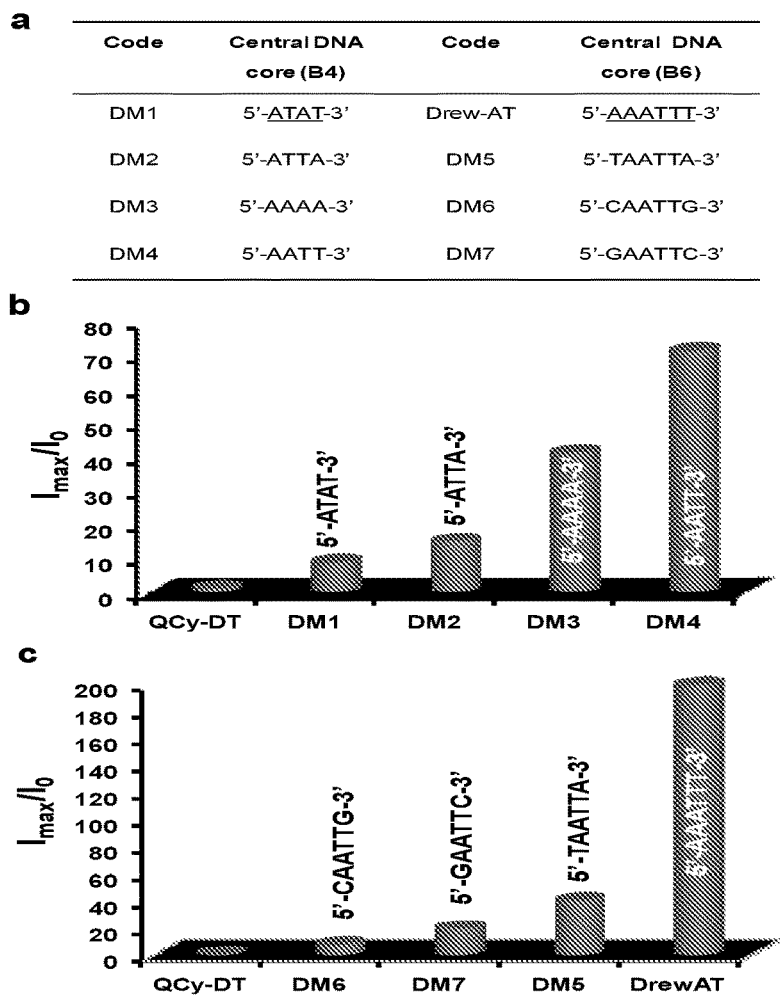
FIG. 5 depicts sequence-specific recognition of AT-rich DNA minor groove by QCy-DT. (a) Table comprises the DNA sequences used in this study and DNA-sequence represents the following sequence of 5'-GCGC-Bn-GCGC-3', where B is nucleobase with n=4, 6 is AT-rich central core.

Almost about ~4-folds difference in fluorescence enhancement of QCy-DT in the presence of (A-T)$_{20}$ compared to self-complementary, alternative AT-base pair containing d(ATAT)$_5$ duplex is observed, although both contain total 20 AT base pairs (FIG. 3 and FIG. 12a). This finding hints at the highly sequence-specific recognition ability of QCy-DT for a specific combination of AT-base pairs in DNA duplex. There are no NIR-fluorescence probes that sequence-specifically recognize the minor groove of AT-rich DNA. The possible sequence-selectivity among AT-base pairs and the typical length of the bent shaped QCy-DT resulted in investigating its ability to bind with a specific combination of AT-sequence with a sequence length of four base pairs. For this purpose, four DNA duplexes with variable (A/T)$_4$ base pairs such as 5'-ATAT-3' (DM1), 5'-ATTA-3' (DM2), 5'-AAAA-3' (DM3) and 5'-AATT-3' (DM4) at the central core is designed (FIG. 5a). QCy-DT showed ~8, ~15, ~40 and ~72-folds fluorescence enhancement in the presence of DM1, DM2, DM3 and DM4 with 5'-ATAT-3', 5'-ATTA-3', 5'-AAAA-3' and 5'-AATT-3' core sequences, respectively, with promising blue shift ($\Lambda_{max}$=~32 nm) in fluorescence maxima (FIG. 5b and FIG. 18a). Interestingly, QCy-DT showed the highest and lowest fluorescence enhancement in the presence of DM4 (5'-AATT-3') and DM1 (5'-ATAT-3'), respectively. Here, "minor groove width" is one of the key parameters that dictate the sequence-selective binding ability of small molecules in the presence of variable (A/T)-rich sequences, depending on their base pair roll. Among all the variable (A/T)$_4$-sequences, 5'-AATT-3' and 5'-ATAT-3' are the two sequences that exhibit narrower and wider minor groove width with zero and large base pair roll, respectively. Therefore, it can be correlated that the present probe QCy-DT recognizes the AT-rich sequences of a DNA duplex. Further, QCy-DT detects all AT-rich sequences by showing varied fluorescence/sensitivity. Also, QCy-DT more particularly shows enhanced sensitivity towards narrow minor groove width of 5'-AATT-3' sequence in a DNA duplex, which favors fluorescence enhancement through the restriction of intramolecular rotation of QCy-DT compared to the relatively wider groove of 5'-ATAT-3' sequence. These results clearly establish the sequence sensitivity of the probe QCy-DT towards AT-rich sequences. Also, the present results clearly prove the high sequence sensitivity of QCy-DT to the variation of (A/T)$_4$ base pairs as the width and interactions vary in the minor groove. This experiment further establishes the enhanced sensitivity of QCy-DT in recognizing AT-rich DNA duplex minor groove containing 5'-AATT-3' sequence.

To understand finer details of the interactions of QCy-DT with local variations around 5'-AATT-3' sequence in the minor groove of DNA duplex, fluorescence studies are performed in the presence of DNA containing core hexanucleotide sequences such as 5'-X(AATT)Y-3' (where X=A/T/G/C and Y is complementary base of X) (FIG. 5a). QCy-DT, in the presence of DNAs containing 5'-GAATTC-3' and 5'-CAATTG-3' cores, showed very weak fluorescence enhancement. Remarkably, enormous fluorescence enhancement is observed in the presence of DNA with 5'-AAATTT-3' core, which is ~4-folds higher than the DNA with 5'-AATT-3' core sequence alone. Surprisingly, replacing A with T at X in 5'-X(AATT)Y-3' sequence reduced the fluorescence enhancement of QCy-DT, which is ~1.5-folds lesser than 5'-AATT-3' sequence (FIG. 5c and FIG. 18b). To validate these findings, extensive computational calculations is further carried out using DFT with localized basis to find that optical transitions in these systems occur between two states where charges are transferred from the DNA double helix to the bound molecule in the minor groove. In the case of QCy-DT binding to 5'-AAATTT-3', the emission is dictated by complete charge transfer from the first adenine to the bound molecule, forming a strong dipolar matrix. For the 5'-TAATTA-3', the first thymine does not contribute to the emission. However, in the latter case, the optical transition results into two states with weak transition dipoles, thereby giving broad emission spectra (FIG. 19 and FIG. 20).

Example 7

Fluorescence Imaging, Cytotoxicity Studies and Photostability of Compound QCy-DT Fluorescence Study in Live Cells MCF-7 cells are propagated on 20 mm cover slips in a 6-well plate in DMEM medium supplemented with 10% fetal bovine serum at about 37° C. in a humidified atmosphere containing 5% $CO_2$ till 80% confluency is achieved. Cells are incubated for about 60 min with probe QCy-DT (resuspended in Mili-Q water) at various concentrations (0.5 µM and 1 µM) in a humidified $CO_2$ incubator at about 37° C. Milli-Q water is used as a vehicle control. Following the treatment, fluorescence microscopy is performed using Carl Zeiss AXIO Imager Z1 and the software used for image capturing is AxioVision Rel. 4.8.

Fluorescence Study in Fixed Cells

HeLa cells are grown on the cover slip for about 24 hours in DMEM medium supplemented with 10% fetal bovine serum at about 37° C. in a humidified atmosphere containing 5% $CO_2$ till 80% confluency is achieved. Then cells are fixed with 4% paraformaldehyde in PBS for 10 min. After rinsing twice with PBS, HeLa cells are treated separately with probe QCy-DT at various concentrations (0.5 µM and 1 µM) for 10 min at room temperature. Subsequently, cover slips are incubated with Hoechst 33258 at 10 µg/mL for nuclear staining. Fluorescence images are taken by Carl Zeiss Laser Scanning Microscope (LSM510 META).

Cell Viability Assay

MCF-7 cells (4×10$^3$ cells/well) are seeded in 96-well plate (flat bottom) and cultured for 12 hours. Following this, cells are treated with 2, 4 and 8 M of probe QCy-DT respectively for about 72 hours and further incubated in a humidified $CO_2$ incubator at about 37° C. 20 µL of MTT (5 mg/mL in PBS) solution is added to each well and incubated for about 4 hours at about 37° C. in the $CO_2$ incubator. DMSO (200 µL)

is then added to each well. After about 1 hour, absorbance is taken in ELISA microplate reader at 570 nm wavelength.

Following formula is applied for the calculation of percentage of cell viability (CV):

CV=(absorbance of the experimental samples/absorbance of the control sample)×100

The data is normalized with control and plotted with mean and standard error.

Photostability Assay in MCF-7 by Confocal Fluorescence Microscopy Imaging

MCF-7 Cells are propagated on 20 mm cover slips in a 6-well plate in DMEM medium supplemented with 10% fetal bovine serum at about 37° C. in a humidified atmosphere containing 5% $CO_2$ till 80% confluency is achieved. Cells are incubated for a duration of about 60 min with probe QCy-DT (resuspended in Mili-Q water) at 2 µM concentration in a humidified $CO_2$ incubator at about 37° C. Following treatment, the photostability of QCy-DT is measured by continuous scanning using OLYMPUS FV1000 confocal fluorescence microscope, under 568 nm line of an Argon ion laser for different time durations of about 10 sec, 120 sec and 300 sec. Olympus Fluoview software is used to quantitatively investigate the intensity of signals of QCy-DT at zero time points and after photo bleaching. The data is plotted with mean and standard error.

Results

Sequence-specific recognition of AT-rich DNA minor groove by switch-on NIR-fluorescence of QCy-DT resulted in further studies on its cellular uptake and applications in nuclear DNA staining. In order to check its permeability, cellular uptake studies are carried out in live and fixed conditions of MCF-7 and HeLa cells, respectively. First, MCF-7 cells are incubated with probe QCy-DT (0.5 and 1 µM) without fixing, and live cell imaging is conducted using Carl Zeiss fluorescence microscope as described above. Fluorescence imaging of MCF-7 cells with QCy-DT showed selective staining of the cell nucleus by the probe, confirming that QCy-DT is cell membrane-permeable molecule that confers selective staining of the nucleus (FIG. 6a-d and FIG. 21a-b). Next, HeLa cells are fixed and incubated with QCy-DT (0.5 and 1 µM) along with Hoechst as the control nuclear staining dye. Fluorescence images showed selective staining of the cell nucleus, and remarkable co-localization with Hoechst dye (FIG. 6e-h and FIG. 21e-h). Further, cells showed the pattern of black nucleoli, which is a characteristic feature of specific DNA minor groove binders over single-strand DNA and RNAs. Therefore, staining results obtained with live and fixed cells confirmed high cell permeability, efficiency (low staining concentration of 1 µM), and preferential targeting of cell nuclear DNA.

Cytotoxicity is a major constraint with several DNA binding probes. To investigate the cytotoxicity of QCy-DT, cell viability assay (MTT assay) is performed in MCF-7 cells after incubation of about 72 hours. It is observed that up to 8 µM of QCy-DT, >76% cell viability is retained over a treatment period of more than about 72 hours (FIG. 22a) suggesting low-toxicity of QCy-DT.

Another important criterion for a fluorescent molecule to be used as a probe for cell imaging applications is its stability upon excitation. To evaluate whether the cells could sustain the excitation of an argon ion laser and still provide a fluorescent signal bright enough for cell imaging, photostability assay is performed for QCy-DT in MCF-7 cells. After continuous 120-second argon ion laser excitation at 568 nm, QCy-DT exhibited a remainder fluorescence intensity of ~80%. Also, ~50% fluorescent signal intensity could be detected even after 300 sec excitation (FIG. 22b). Overall, cell staining and viability assays confirmed the low-toxicity, cell permeability, photostability and selective nuclear targeting ability of QCy-DT.

Example 7

Plasmodium falciparum Culture, Synchronization and Treatment of Malaria Parasites with Compound QCy-DT P. falciparum strain 3D7 is cultured. Briefly, malaria parasites are cultured in human erythrocytes in T75 flasks with RPMI 1640 (Gibco) supplemented with 10 µg/mL gentamicin (Sigma), 50 µg/mL ampicillin, 0.2% $NaHCO_3$ (Sigma), 0.5% albumax (Invitrogen) and Hypoxanthine (27 mg/L). The culture is maintained under standard conditions (37° C. in 90% nitrogen, 5% $CO_2$, and 5% $O_2$). For synchronization of the parasites, ring-staged parasites are treated with 5% sorbitol at 37° C. for about 5-10 min, followed by washing with pre-warmed incomplete medium twice, and placed back in complete medium. QCy-DT probe (resuspended in Mili-Q water) is added to parasites (25±2 hpi) at a final concentration of 0.5 µM and the parasites are incubated for 30 min at 37° C. Following treatment fluorescence imaging of the parasites is performed using Carl Zeiss AXIO Imager Z1 and the software used for image capturing was AxioVision Rel. 4.8.

$IC_{50}$ Determination in Malaria Parasites

To determine the $IC_{50}$ value of QCy-DT against P. falciparum, parasites are synchronized in ring stage (~12±2 h) and parasitemia is maintained at ~1%, followed by treatment with 0, 0.5, 1, 2 and 4 µM of QCy-DT at early trophozoite stage (~20±2 h). After about 40 hours of the QCy-DT treatment, Geimsa stained slides are prepared, and parasitemia is counted. At least six homogenous microscopic fields are counted for each treatment, and each experiment is done in triplicates. The graphs are plotted for the percentage of parasitemia (at 0 time point and at 40 hours after incubation with QCy-DT) against QCy-DT concentration, with mean and standard error.

Results:

Plasmodium falciparum is selected as a model system to confirm the selectivity of probe QCy-DT towards AT-rich dsDNA in cellular environment as the malarial parasite possesses a genome exceptionally rich in AT-base pairs (~80%). It will also help us to determine whether QCy-DT has any detrimental effect on Plasmodium parasites. The parasites are incubated with 0.5 µM concentration of probe QCy-DT at early trophozoite stage. Live fluorescence imaging of these parasites showed that probe QCy-DT could specifically stain the parasite nuclei, but not the cytosolic part of the parasite or red blood cells (RBC) (FIG. 7a-d). These results clearly indicate that probe QCy-DT binds to the AT-rich genome of the parasite at low concentrations. Also, uptake by malaria parasites and specific enrichment of the probe QCy-DT within the nucleus of the parasites indicate the possibility of the molecule's potential to interfere with the DNA metabolism of P. falciparum. To assess the inhibitory action of QCy-DT in malarial parasites, $IC_{50}$ of the probe QCy-DT is determined by treating early trophozoite stage P. falciparum (when DNA replication initiates) and the parasites are followed for the next cycle when new rings are formed. $IC_{50}$ for QCy-DT against P. falciparum parasites is found to be <4 µM (FIG. 7e). It is observed that parasites are arrested in the trophozoite stage and could not form rings in the following cycle at a higher concentration of 8 µM. The arrest of the cells during trophozoite stage establishes that the uptake of QCy-DT in the parasite nucleus may abrogate the process of DNA replication.

In addition to QCy-DT, other Formula I compounds also show similar physical & chemical characteristics, and biological activity results when studies including studies related to photophysical properties, switch-on NIR-fluorescence in the presence of DNA, base pair-specific recognition and switch-on fluorescence in the presence of DNA, Binding Stoichiometry, Affinity and Quantum Yield of drug molecules for DNA Duplexes, AT-rich DNA Recognition, Sequence-Specific Recognition of DNA, Fluorescence Imaging, Cytotoxicity Studies and photostability are performed.

The present disclosure thus demonstrates the unique sequence-specific and minor groove recognition properties of the designed NIR fluorescence probes of Formula I for AT-rich DNA. In particular, the compound of Formula I possesses a distinctive ICT process responsible for the NIR fluorescence. The inherent non-fluorescent behavior of compound of Formula I in unbound-state and switch-on fluorescence in the bound-state makes it a versatile DNA probe. Fluorescence studies of compound of Formula I demonstrates its selective fluorescence enhancement in the presence of AT-rich duplexes over GC-rich DNA, single-stranded DNA and RNA. Circular dichroism studies confirm the selective minor groove recognition of AT-rich DNA, which induces the characteristic CD signal to compound of Formula I. Computational studies further support the minor groove recognition of AT-rich DNA in which the positively charged edge of Formula I eg. QCy-DT is located inside the minor groove of DNA. Fluorescence studies of variable (A/T)$_4$ base pairs containing DNA duplexes reveal sequence-specific fluorescence enhancement in the presence of 5'-AATT-3'. Furthermore, experiments on the local variations around 5'-X(AATT)Y-3' confirm that X=A and Y=T (i.e., 5'-AAATTT-3') is the most preferred sequence for depicting maximum fluorescence enhancement of compound of Formula I.

Further, confocal fluorescence imaging and cell viability studies of MCF-7 and HeLa cells show effective cell permeability, low-toxicity and selective staining of nuclear DNA both in live and fixed cell lines. Selective nuclear staining of parasites such as *P. falciparum* and inhibition of its growth and propagation by compound of Formula I proves Formula I compounds as potential therapeutic agent against parasitic infections similar to other minor groove binders. Remarkably, the IC$_{50}$ value for *Plasmodium* parasites (<about 4 micromolar) is considerably low. Thus, the aspects related to ease of synthesis, switch-on NIR-fluorescence, large Stokes shift, cell permeability, low-toxicity, cell imaging of both live and fixed cells, and parasite staining makes the Formula I compounds practically viable, inexpensive and a superior DNA probe compared to commercially available dyes routinely used.

The Formula I compounds of the present disclosure have several applications including but not limiting to: (a) these dyes can be used as (NIR) fluorescence binding markers for biomolecules like DNA and protein; (b) these fluorescence dyes are useful for sequence specific recognition of dsDNA and in treating gene-related human diseases especially cancer, parasitic and viral infections; (c) the intrinsic fluorescence property of these dyes makes them a versatile fluorescence marker for molecular biology and immunohistochemistry, fluorescence spectroscopy and microscopy, flow cytometry and DNA quantification applications; (d) choosing suitable donors leads to the formation of an efficient FRET-pairs which are useful for monitoring the conformational changes in nucleic acids and proteins; (e) detection and inhibition of parasites and corresponding infections caused by microorganisms comprising rich AT-content; (f) designing new enzymatic or chemically triggered self-immolative theranostic prodrugs for abnormal cells; and (g) applications in the field of diagnostics and therapeutics targeting DNA and related biomolecules.

We claim:

1. A compound of Formula I:

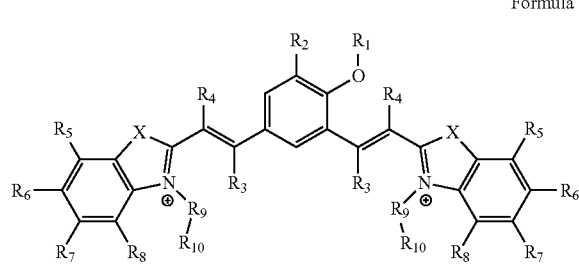

Formula I wherein:
- X is selected from the group consisting of oxygen, sulphur, and selenium;
- $R_1$, $R_2$, $R_3$, $R_4$, $R_5$, $R_6$, $R_7$, and $R_8$ are hydrogen;
- '$R_9$' is selected from the group consisting of H and —$(CH_2)_n$—, wherein 'n' is 1-6;
- '$R_{10}$' is selected from the group consisting of hydrogen, —OH, methyl, amine, terminal alkyne, alkene, alkyl acid, amine acid, and sulfonates ($SO_3^-$).

2. The compound of claim 1, wherein the compound of formula 1 binds to AT rich sequences in DNA.

3. The compound of Formula I selected from a group consisting of:

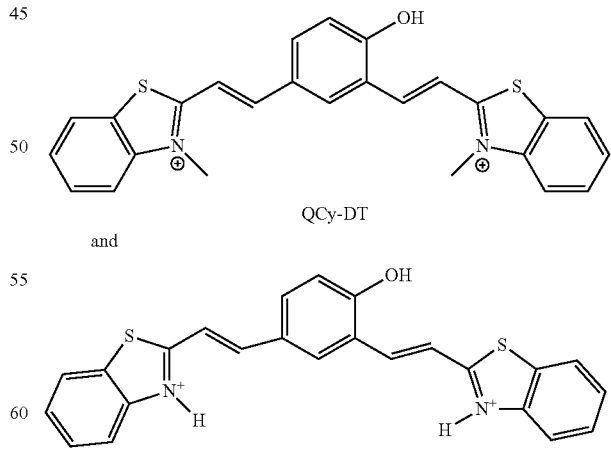

QCy-DT and

4. A process for the preparation of a compound of Formula I according to claim 1, the process comprising:

a. reacting a compound of Formula II with a compound of Formula III to obtain a compound of Formula IV

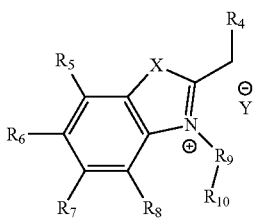

Formula IV wherein,
$R_4$, $R_5$, $R_6$, $R_7$, and $R_8$ are H;
$R_9$ is H or —$(CH_2)_n$—, wherein 'n' is 1-6;
$R_{10}$ is selected from a group comprising hydrogen, —OH, methyl, amine, terminal alkyne, alkene, alkyl acid, amine acid and sulfonates ($SO_3^-$); and
Y is Br or I;

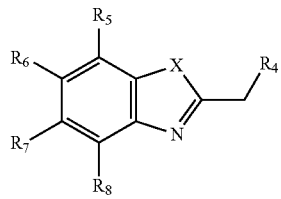

Formula II

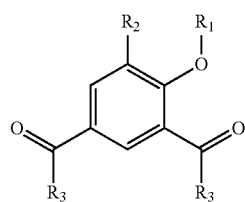

Formula III

Y = Br or I and
b. reacting the compound of Formula IV with a compound of Formula V in the presence of piperidine and alcohol, Formula V wherein,
$R_1$, $R_2$, and $R_3$ are H.

5. The process of claim 4, wherein the compound is quinone cyanine-dithiazole, QCy-DT prepared by:
a. reacting 2-methyl benzothiazole with methyl iodide to obtain N-methyl-2-methylbenzothiazole; and
b. reacting the N-methyl-2-methylbenzothiazole with 4-hydroxyisophthalaldehyde in presence of piperidine.

6. The process as claimed in claim 4, wherein said process is carried out at a temperature ranging from about 30° C. to 100° C., and for a time period ranging from about 2 hours to 24 hours; and wherein said the steps a) and b) further comprise isolation, purification or a combination thereof of the corresponding product; wherein said isolation and purification is carried out by acts selected from a group comprising addition of solvent, washing with solvent, quenching, filtration, extraction, chromatography and combinations thereof.

7. A pharmaceutical composition comprising the compound of Formula I of claim 1,
optionally along with at least one pharmaceutically acceptable excipient.

8. The pharmaceutical composition of claim 7, wherein the compound is selected from the group consisting of:

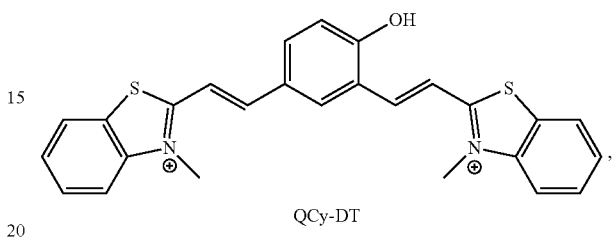

QCy-DT and
wherein the pharmaceutically acceptable excipient is selected from a group comprising adjuvant, diluent, carrier, granulating agents, binding agents, lubricating agents, disintegrating agent, sweetening agents, glidant, anti-adherent, anti-static agent, surfactant, antioxidant, gum, coating agent, coloring agent, flavouring agent, coating agent, plasticizer, preservative, suspending agent, emulsifying agent, plant cellulosic material, spheronization agent, other conventionally known pharmaceutically acceptable excipient or any combination of excipients thereof; and the composition is administered to a subject through modes selected from a group comprising intravenous administration, intramuscular administration, intraperitoneal administration, hepatoportal administration, intra articular administration and pancreatic duodenal artery administration, or any combination thereof.

9. A method of detection or quantification of DNA sequence, said method comprising:
a. contacting the compound of Formula I of claim 1 with a DNA sequence so as to allow for hybridization of the compound of formula I with the DNA sequence; and
b. detecting or quantifying the binding intensity by measuring the change in fluorescence of the compound resulting from the specific interaction or binding of the compound to the DNA sequence, upon hybridization of the compound with the DNA sequence.

10. The method as claimed in claim 9, wherein the method is for detecting the DNA sequence which is an AT rich sequence in a eukaryotic cell selected from the group consisting of cancerous cells infected with microorganisms, unicellular protozoan, parasite, and other abnormal cells.

11. The method as claimed in claim 9, wherein the specific interaction or binding is in the minor groove of the DNA sequence, and wherein the compound delocalizes pi electrons between donor acceptor atoms on binding to the minor groove of the DNA sequence and wherein the specific interaction or binding is by base pairing, covalent or non-covalent interaction, resulting in the fluorescence.

12. A method of inhibiting growth of a cell, said method comprising contacting the compound of Formula I of claim 1 with the cell.

13. The method of claim 12, wherein the cell is an eukaryotic cell selected from the group consisting of cancerous cells, cells infected with microorganisms, parasite or unicellular protozoan, and other abnormal cells, and wherein the parasite is *Plasmodium* selected from the group consisting of *Plasmodium falciparum, Plasmodium vivax, Plasmodium ovale*, and *Plasmodium malariae.*

14. A method of diagnosing disease characterized by the presence of a specific DNA sequence or abnormal levels of AT rich DNA, the method comprising:
   a. contacting the of compound of Formula I of claim 1 with a biological sample comprising the DNA sequence to allow for hybridization of the compound with the DNA sequence;
   b. removing unhybridized compound from the mixture; and
   c. detecting or quantifying the presence of the specific DNA sequence, by measuring a change in fluorescence of the compound resulting from the specific interaction or binding of the compound to the DNA sequence, upon hybridization of the compound to the DNA.

\* \* \* \* \*

SEQUENCE LISTING

```
<160> NUMBER OF SEQ ID NOS: 26

<210> SEQ ID NO 1
<211> LENGTH: 14
<212> TYPE: DNA
<213> ORGANISM: Artificial Sequence
<220> FEATURE:
<223> OTHER INFORMATION: AT/GC duplex

<400> SEQUENCE: 1
gcgcaaattt gcgc                                                     14

<210> SEQ ID NO 2
<211> LENGTH: 14
<212> TYPE: DNA
<213> ORGANISM: Artificial Sequence
<220> FEATURE:
<223> OTHER INFORMATION: AT/GC duplex

<400> SEQUENCE: 2
cgcgtttaaa cgcg                                                     14

<210> SEQ ID NO 3
<211> LENGTH: 20
<212> TYPE: DNA
<213> ORGANISM: Artificial Sequence
```

```
<220> FEATURE:
<223> OTHER INFORMATION: AT/GC duplex

<400> SEQUENCE: 3
aaaaaaaaaa aaaaaaaaaa                                               20

<210> SEQ ID NO 4
<211> LENGTH: 20
<212> TYPE: DNA
<213> ORGANISM: Artificial Sequence
<220> FEATURE:
<223> OTHER INFORMATION: AT/GC duplex

<400> SEQUENCE: 4
tttttttttt tttttttttt                                               20

<210> SEQ ID NO 5
<211> LENGTH: 20
<212> TYPE: DNA
<213> ORGANISM: Artificial Sequence
<220> FEATURE:
<223> OTHER INFORMATION: AT/GC duplex

<400> SEQUENCE: 5
atatatatat atatatatat                                               20

<210> SEQ ID NO 6
<211> LENGTH: 20
<212> TYPE: DNA
<213> ORGANISM: Artificial Sequence
<220> FEATURE:
<223> OTHER INFORMATION: AT/GC duplex

<400> SEQUENCE: 6
tatatatata tatatatata                                               20

<210> SEQ ID NO 7
<211> LENGTH: 20
<212> TYPE: DNA
<213> ORGANISM: Artificial Sequence
<220> FEATURE:
<223> OTHER INFORMATION: AT/GC dulplex

<400> SEQUENCE: 7
gggggggggg gggggggggg                                               20

<210> SEQ ID NO 8
<211> LENGTH: 22
<212> TYPE: DNA
<213> ORGANISM: Artificial Sequence
<220> FEATURE:
<223> OTHER INFORMATION: AT/GC duplex

<400> SEQUENCE: 8
cccccccccc cccccccccc cc                                            22

<210> SEQ ID NO 9
<211> LENGTH: 16
<212> TYPE: DNA
<213> ORGANISM: Artificial Sequence
<220> FEATURE:
<223> OTHER INFORMATION: AT/GC duplex

<400> SEQUENCE: 9
cgataagcgc ttatcg                                                   16
```

```
<210> SEQ ID NO 10
<211> LENGTH: 16
<212> TYPE: DNA
<213> ORGANISM: Artificial Sequence
<220> FEATURE:
<223> OTHER INFORMATION: AT/GC duplex

<400> SEQUENCE: 10
gctattcgcg aatagc                                                        16

<210> SEQ ID NO 11
<211> LENGTH: 6
<212> TYPE: DNA
<213> ORGANISM: Artificial Sequence
<220> FEATURE:
<223> OTHER INFORMATION: AT rich

<400> SEQUENCE: 11 aaattt                                                                    6

<210> SEQ ID NO 12
<211> LENGTH: 6
<212> TYPE: DNA
<213> ORGANISM: Artificial Sequence
<220> FEATURE:
<223> OTHER INFORMATION: AT rich

<400> SEQUENCE: 12 tttaaa                                                                    6

<210> SEQ ID NO 13
<211> LENGTH: 6
<212> TYPE: DNA
<213> ORGANISM: Artificial Sequence
<220> FEATURE:
<223> OTHER INFORMATION: A/T rich

<400> SEQUENCE: 13 aaaaaa                                                                    6

<210> SEQ ID NO 14
<211> LENGTH: 6
<212> TYPE: DNA
<213> ORGANISM: Artificial Sequence
<220> FEATURE:
<223> OTHER INFORMATION: A/T rich

<400> SEQUENCE: 14 tttttt                                                                    6

<210> SEQ ID NO 15
<211> LENGTH: 6
<212> TYPE: DNA
<213> ORGANISM: Artificial Sequence
<220> FEATURE:
<223> OTHER INFORMATION: GC rich

<400> SEQUENCE: 15 gcgcgc                                                                    6

<210> SEQ ID NO 16
<211> LENGTH: 6
<212> TYPE: DNA
<213> ORGANISM: Artificial Sequence
<220> FEATURE:
<223> OTHER INFORMATION: GC rich
```

<400> SEQUENCE: 16 cgcgcg                                                                     6

<210> SEQ ID NO 17
<211> LENGTH: 6
<212> TYPE: DNA
<213> ORGANISM: Artificial Sequence
<220> FEATURE:
<223> OTHER INFORMATION: G/C rich

<400> SEQUENCE: 17 gggggg                                                                     6

<210> SEQ ID NO 18
<211> LENGTH: 6
<212> TYPE: DNA
<213> ORGANISM: Artificial Sequence
<220> FEATURE:
<223> OTHER INFORMATION: G/C rich

<400> SEQUENCE: 18 cccccc                                                                     6

<210> SEQ ID NO 19
<211> LENGTH: 4
<212> TYPE: DNA
<213> ORGANISM: Artificial Sequence
<220> FEATURE:
<223> OTHER INFORMATION: DM1

<400> SEQUENCE: 19 atat                                                                       4

<210> SEQ ID NO 20
<211> LENGTH: 4
<212> TYPE: DNA
<213> ORGANISM: Artificial Sequence
<220> FEATURE:
<223> OTHER INFORMATION: DM2

<400> SEQUENCE: 20 atta                                                                       4

<210> SEQ ID NO 21
<211> LENGTH: 4
<212> TYPE: DNA
<213> ORGANISM: Artificial Sequence
<220> FEATURE:
<223> OTHER INFORMATION: DM3

<400> SEQUENCE: 21 aaaa                                                                       4

<210> SEQ ID NO 22
<211> LENGTH: 4
<212> TYPE: DNA
<213> ORGANISM: Artificial Sequence
<220> FEATURE:
<223> OTHER INFORMATION: DM4

<400> SEQUENCE: 22 aatt                                                                       4

<210> SEQ ID NO 23

```
<211> LENGTH: 6
<212> TYPE: DNA
<213> ORGANISM: Artificial Sequence
<220> FEATURE:
<223> OTHER INFORMATION: Drew-AT

<400> SEQUENCE: 23 aaattt                                                                  6

<210> SEQ ID NO 24
<211> LENGTH: 6
<212> TYPE: DNA
<213> ORGANISM: Artificial Sequence
<220> FEATURE:
<223> OTHER INFORMATION: DM5

<400> SEQUENCE: 24 taatta                                                                  6

<210> SEQ ID NO 25
<211> LENGTH: 6
<212> TYPE: DNA
<213> ORGANISM: Artificial Sequence
<220> FEATURE:
<223> OTHER INFORMATION: DM6

<400> SEQUENCE: 25 caattg                                                                  6

<210> SEQ ID NO 26
<211> LENGTH: 6
<212> TYPE: DNA
<213> ORGANISM: Artificial Sequence
<220> FEATURE:
<223> OTHER INFORMATION: DM7

<400> SEQUENCE: 26 gaattc                                                                  6
```